United States Patent
Matsumoto et al.

(10) Patent No.: US 12,017,977 B2
(45) Date of Patent: Jun. 25, 2024

(54) METHOD FOR PRODUCING CARBODIIMIDE COMPOUND

(71) Applicant: NISSHINBO CHEMICAL INC., Tokyo (JP)

(72) Inventors: Nobuyuki Matsumoto, Chiba (JP); Kenichi Yanagisawa, Chiba (JP)

(73) Assignee: NISSHINBO CHEMICAL INC., Tokyo (JP)

(*) Notice: Subject to any disclaimer, the term of this patent is extended or adjusted under 35 U.S.C. 154(b) by 0 days.

(21) Appl. No.: 18/075,488

(22) Filed: Dec. 6, 2022

(65) Prior Publication Data

US 2023/0106672 A1 Apr. 6, 2023

Related U.S. Application Data

(63) Continuation of application No. 16/979,484, filed as application No. PCT/JP2019/009934 on Mar. 12, 2019.

(30) Foreign Application Priority Data

Mar. 12, 2018 (JP) ................. 2018-044526

(51) Int. Cl.
| | | |
|---|---|---|
| C07C 269/02 | (2006.01) | |
| B01J 31/04 | (2006.01) | |
| B01J 31/08 | (2006.01) | |
| B01J 31/12 | (2006.01) | |
| C07C 267/00 | (2006.01) | |
| C08G 18/02 | (2006.01) | |
| C08G 18/76 | (2006.01) | |
| C08G 18/79 | (2006.01) | |
| C08G 18/81 | (2006.01) | |
| C08K 5/29 | (2006.01) | |
| C08L 75/06 | (2006.01) | |

(52) U.S. Cl.
CPC .............. *C07C 267/00* (2013.01); *B01J 31/04* (2013.01); *B01J 31/08* (2013.01); *B01J 31/12* (2013.01); *C07C 269/02* (2013.01); *C08G 18/025* (2013.01); *C08G 18/7628* (2013.01); *C08G 18/797* (2013.01); *C08G 18/8108* (2013.01); *C08K 5/29* (2013.01); *C08L 75/06* (2013.01)

(58) Field of Classification Search
CPC .................. C07C 269/02; C08G 18/797
See application file for complete search history.

(56) References Cited

U.S. PATENT DOCUMENTS

| | | | | |
|---|---|---|---|---|
| 3,320,309 | A | * 5/1967 | Schlack | ............... C07C 267/00 564/252 |
| 3,345,407 | A | * 10/1967 | Tucker | ................. C07C 267/00 564/252 |
| 3,426,025 | A | 2/1969 | Smeltz | |
| 3,929,733 | A | 12/1975 | Alberino et al. | |
| 5,688,875 | A | 11/1997 | Sasaki et al. | |
| 5,958,516 | A | 9/1999 | Imashiro et al. | |
| 6,184,410 | B1 | 2/2001 | Bollmann et al. | |
| 6,395,824 | B1 | 5/2002 | Beutler et al. | |
| 2007/0208158 | A1 | 9/2007 | Kramer | |
| 2009/0156778 | A1* | 6/2009 | Brahm | ................. C07D 251/34 528/59 |
| 2010/0093888 | A1 | 4/2010 | Endo et al. | |
| 2013/0144666 | A1 | 6/2013 | Derksen et al. | |
| 2017/0088509 | A1 | 3/2017 | Laufer et al. | |

FOREIGN PATENT DOCUMENTS

| | | |
|---|---|---|
| CA | 2 989 239 A1 | 12/2016 |
| CN | 103119084 A | 5/2013 |
| GB | 1 404 822 A | 9/1975 |
| GB | 1 515 523 A | 8/1978 |
| JP | 50-159593 A | 12/1975 |
| JP | 51-37996 A | 3/1976 |
| JP | 51-81599 A | 5/1976 |
| JP | 7-330849 A | 12/1995 |
| JP | 8-59303 A | 3/1996 |
| JP | 9-124582 A | 5/1997 |
| JP | 9-136869 A | 8/1997 |
| JP | 2013-193986 A | 9/2013 |
| JP | 2017-522279 A | 8/2017 |

OTHER PUBLICATIONS

"Synthesis of Reaction of Drugs." China Press of Traditional Medicine, Aug. 2017, pp. 1-2 and 323-326 (14 pages total), with English translation.
Chinese Office Action and Search Report for Chinese Application No. 201980018183.0, dated Feb. 22, 2022.
Extended European Search Report for European Application No. 19766631.8, dated Nov. 26, 2021.
International Search Report for PCT/JP2019/009934 (PCT/ISA/210) mailed on Jun. 11, 2019.
Luo et al., "Catalyst for Isocyanate Condensation Carbodiimide Catalyst," Polyurethane Industry, vol. 19, No. 6, 2004, 4 pages, with English abstract.

\* cited by examiner

*Primary Examiner* — Michael L Leonard
(74) *Attorney, Agent, or Firm* — Birch, Stewart, Kolasch & Birch, LLP

(57) ABSTRACT

A method for producing a carbodiimide compound, comprising a carbodiimide production step of reacting an aliphatic tertiary isocyanate compound (A) in the presence of an organic alkali metal compound (B) having Lewis basicity.

8 Claims, No Drawings

METHOD FOR PRODUCING CARBODIIMIDE COMPOUND

CROSS-REFERENCE TO RELATED APPLICATIONS

This application is a Continuation application of co-pending application Ser. No. 16/979,484, filed on Sep. 9, 2020, which is the National Phase under 35 U.S.C. § 371 of International Application No. PCT/JP2019/009934, filed on Mar. 12, 2019, which claims the benefit under 35 U.S.C. § 119(a) to Patent Application No. 2018-044526, filed in Japan on Mar. 12, 2018, all of which are hereby expressly incorporated by reference into the present application.

TECHNICAL FIELD

The present invention relates to a method for producing a carbodiimide compound, particularly relates to a method for producing a carbodiimide compound from isocyanate. The present invention also relates to a method for producing a polyurethane, use of a carbodiimide compound, a carbodiimide composition, a stabilizer, and an ester-based resin composition.

BACKGROUND ART

Carbodiimide compounds are useful for various applications, such as stabilizers and hydrolysis inhibitors for various resins such as thermoplastic resins.

It is known to use organic phosphorus catalysts as carbodiimidization catalysts in the production of carbodiimide compounds from isocyanates.

For example, PTL 1 describes formation of a polyisocyanate carbodiimide by reacting a polyisocyanate in the presence of a phosphorus-containing catalyst.

Examples of a carbodiimide formation catalyst in PTL 2 include 1-phenyl-2-phospholene-1-oxide, 3-methyl-1-phenyl-2-phospholene-1-oxide, 1-phenyl phospholene-1-sulfide, 1-ethyl-2-phospholene-1-oxide, 1-ethyl-3-methyl phospholene-1-oxide, and corresponding isomers 3-phospholenes.

It is also known to use organic metal compounds as isocyanuration catalysts in the modification of isocyanates with isocyanurates.

For example, PTL 3 describes use of a carboxylic acid alkali metal salt and a tertiary amine for a catalyst for aiding a trimerization reaction (isocyanuration reaction) of isocyanate. Examples of the carboxylic acid alkali metal salt listed in the PTL include carboxylic acid alkali metal salts such as sodium acetate, potassium acetate, potassium 2-ethylhexoate, potassium adipate, and sodium benzoate. Examples of the tertiary amine listed in the PTL include N-alkylethyleneimine, N-(2-dimethylaminoethyl)-N'-methylpiperazine, and tris-3-dimethylaminopropylhexahydro-s-triazine.

CITATION LIST

Patent Literatures

PTL 1: JP 51-37996 A
PTL 2: JP 51-61599 A
PTL 3: JP 50-159593 A

SUMMARY OF INVENTION

Technical Problem

An organic phosphorus compound used as a carbodiimidization catalyst in each of PTLs 1 and 2 is a very expensive compound.

When the organic phosphorus compound is used to produce a carbodiimide compound, a problem is that the organic phosphorus compound remaining in the resulting carbodiimide compound interferes with an object material to result in difficulty of use. A known method for solving the problem, in which a catalyst is distilled off under reduced pressure during or after synthesis of a carbodiimide compound, has the problem of causing a process to be complicated.

The present invention has been made for solving the above problems, and an object thereof is to provide a method for producing a carbodiimide compound from an isocyanate compound at a high yield even in the case of substantial no use of any organic phosphorus compound as a carbodiimidization catalyst, as well as a method for producing a polyurethane, use of a carbodiimide compound, a carbodiimide composition, a stabilizer, and an ester-based resin composition.

Solution to Problem

The present inventors have made intensive studies, and as a result, have found that an organic alkali metal compound among organic metal compounds conventionally utilized as isocyanurate catalysts is useful as a carbodiimidization catalyst to a specified isocyanate and furthermore the catalyst can be removed by a simple method when, if necessary, removed.

That is, the present invention provides the following [1] to [10].

[1] A method for producing a carbodiimide compound, comprising a carbodiimide production step of reacting an aliphatic tertiary isocyanate compound (A) in the presence of an organic alkali metal compound (B) having Lewis basicity.

[2] The method for producing a carbodiimide compound according to [1], wherein the organic alkali metal compound (B) having Lewis basicity is at least one of a metal alkoxide, a metal amide, and a metal carboxylate.

[3] The method for producing a carbodiimide compound according to [1] or [2], wherein the aliphatic tertiary isocyanate compound (A) is a compound in which at least one aromatic ring is bonded to a tertiary carbon atom to which an isocyanate group is bonded.

[4] The method for producing a carbodiimide compound according to any one of [1] to [3], wherein the aliphatic tertiary isocyanate compound (A) is at least one of tetramethylxylylene diisocyanate and 3-isopropenyl-α,α-dimethylbenzyl isocyanate.

[5] The method for producing a carbodiimide compound according to any one of [1] to [4], wherein the aliphatic tertiary isocyanate compound (A) is reacted in the presence of the organic alkali metal compound (B) having Lewis basicity and a phase transfer catalyst (C) in the carbodiimide production step.

[6] The method for producing a carbodiimide compound according to [5], wherein the phase transfer catalyst (C) is at least one of crown ether, a quaternary ammonium salt, and a compound represented by the following general formula (1):

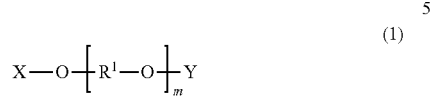 (1)

wherein X and Y are each independently a methyl group, an ethyl group, a propyl group, a butyl group, or a phenyl group; $R^1$ is an alkylene group having 2 to 3 carbon atoms; and m is an integer of 2 to 500.

[7] The method for producing a carbodiimide compound according to any one of [1] to [6], wherein the method comprises an end-capping step of end-capping a portion of an isocyanate group in the aliphatic tertiary isocyanate compound (A) with an end-capping agent at at least one time point among three time points, before the carbodiimide production step, during the production step, and after the production step, and the end-capping agent is a compound (D-1) represented by the following general formula (2-1);

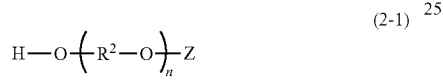 (2-1)

wherein Z is a methyl group, an ethyl group, a propyl group, a butyl group, or a phenyl group; $R^2$ is an alkylene group having 2 to 3 carbon atoms; and n is an integer of 2 to 500.

[8] The method for producing a carbodiimide compound according to any one of [1] to [7], wherein the method comprises a chain extension step of reacting a portion of an isocyanate group in the aliphatic tertiary isocyanate compound (A) with a chain extender at at least one time point among three time points, before the carbodiimide production step, during the production step, and after the production step, and the chain extender is a compound (D-2) represented by the following general formula (2-2);

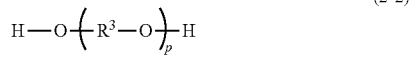 (2-2)

wherein $R^3$ is an alkylene group having 2 to 3 carbon atoms; and p is an integer of 2 to 500.

[9] The method for producing a carbodiimide compound according to any one of [1] to [8], wherein the method comprises an adsorption and removal step of performing adsorption and removal of the organic alkali metal compound (B) having Lewis basicity, with an adsorbent (E), after the carbodiimide production step.

[10] The method for producing a carbodiimide compound according to [9], wherein the adsorbent (E) is at least one of a synthetic aluminum silicate-based adsorbent, synthetic magnesium silicate, an acidic cation-exchange resin, a basic anion-exchange resin, alumina, a silica gel-based adsorbent, a zeolite-based adsorbent, hydrotalcites, a magnesium oxide-aluminum oxide-based solid solution, aluminum hydroxide, magnesium oxide, and an aluminum hydroxide-sodium hydrogen carbonate coprecipitate (dawsonite).

[11] A method for producing a stabilizer having a purity of 90% by mass or more and comprising no phospholene oxides or comprising phospholene oxides at a content of 1 ppm by mass or less, wherein the method comprises the production method according to any one of [1] to [10].

[12] A method for producing a polyurethane, comprising reacting a polyol and a diisocyanate in the presence of a stabilizer to thereby obtain a polyurethane, preferably a thermoplastic polyurethane, wherein
the stabilizer comprises an aliphatic tertiary carbodiimide derived from an aliphatic tertiary isocyanate compound and comprises an alkali metal at a content of less than 2000 ppm by mass.

The method for producing a polyurethane according to [12], wherein an amount of the aliphatic tertiary carbodiimide derived from an aliphatic tertiary isocyanate compound, to be added, based on a total amount of 100 parts by mass of the polyol and the diisocyanate is 0.1 to 2 parts by mass, preferably 0.5 to 1 part by mass.

[14] The method for producing a polyurethane according to [12] or [13], wherein the aliphatic tertiary carbodiimide derived from an aliphatic tertiary isocyanate compound is preferably metered and loaded at a temperature of 20 to 50° C., particularly preferably 25 to 35° C., in the form of a liquid in a continuous or batch manner.

[15] A method for producing a polyurethane, comprising reacting a polyol and a diisocyanate in the presence of a stabilizer to thereby obtain a polyurethane, preferably a thermoplastic polyurethane, wherein
the stabilizer is a carbodiimide compound produced by the method for producing a carbodiimide compound according to any one of [1] to [10].

[16] Use of a carbodiimide compound according to any one of [1] to [10], for prevention of hydrolysis.

[17] A carbodiimide composition comprising a carbodiimide compound with an aliphatic tertiary isocyanate compound (A) as a structural unit, and an alkali metal, and comprising no phospholene oxides or comprising phospholene oxides at a content of 1 ppm by mass or less.

[18] The carbodiimide composition according to [17], further comprising a phase transfer catalyst (C).

[19] A stabilizer comprising a carbodiimide compound with an aliphatic tertiary isocyanate compound (A) as a structural unit, and an alkali metal, and comprising no phospholene oxides or comprising phospholene oxides at a content of 1 ppm by mass or less.

[20] The stabilizer according to [19], further comprising a phase transfer catalyst (C).

[21] An ester-based resin composition comprising the carbodiimide composition according to [17] or [18], and an ester-based resin.

[22] The ester-based resin composition according to [21], comprising the carbodiimide composition at a content of 0.2 to 5.0 parts by mass based on 100 parts by mass of the ester-based resin.

[23] An ester-based resin composition comprising the stabilizer according to [19] or [20], and an ester-based resin.

Advantageous Effects of Invention

According to the present invention, it is possible to produce a carbodiimide compound at a high yield by reacting an aliphatic tertiary isocyanate compound, even in the case of substantial no use of any organic phosphorus compound as a carbodiimidization catalyst.

DESCRIPTION OF EMBODIMENTS

Hereinafter, the present invention will be described with reference to embodiments in detail.

1. Method for Producing Carbodiimide Compound

A method for producing a carbodiimide compound according to the present embodiment comprises a carbodiimide production step of reacting an aliphatic tertiary isocyanate compound (A) in the presence of an organic alkali metal compound (B) having Lewis basicity.

As described above, an organic alkali metal compound usually acts as a catalyst that aids an isocyanate trimerization reaction (isocyanuration reaction). When the aliphatic tertiary isocyanate compound (A) is reacted as isocyanate, however, the organic alkali metal compound (B) having Lewis basicity acts as a carbodiimidization catalyst. Thus, a dimer (uretdione), a trimer (isocyanurate), and any other multimer are inhibited or prevented from being produced, and a carbodiimide compound can be obtained at a high yield.

In the method for producing a carbodiimide compound according to the present embodiment, preferably substantially no organic phosphorus compound is used, more preferably no organic phosphorus compound is use. When no organic phosphorus compound is used, a catalyst removal step performed after carbodiimide production can be omitted, provided that a removal step of any other catalyst may be performed even in no use of any organic phosphorus compound.

The method for producing a carbodiimide compound according to the present embodiment may comprise any step other than the carbodiimide production step. For example, the method may comprise an end-capping step of end-capping a portion of an isocyanate group derived from the aliphatic tertiary isocyanate compound (A) with a compound having a functional group reactive with isocyanate and/or a chain extension step of mutually linking isocyanate, for the purpose of molecular weight control, at at least one time point among three time points, before the carbodiimide production step, during the production step, and after the production step.

For example, when the end-capping step is performed before the production step, a portion of an isocyanate group in the aliphatic tertiary isocyanate compound (A) is preferably end-capped. When the end-capping step is performed during the production step, a portion of a terminal isocyanate group of a polycarbodiimide produced by a carbodiimidization reaction of the aliphatic tertiary isocyanate compound (A) and a portion of an isocyanate group in the aliphatic tertiary isocyanate compound (A) before such a reaction are preferably end-capped. When the end-capping step is performed after polycarbodiimide production, a terminal isocyanate group of a polycarbodiimide compound produced is preferably fully end-capped.

When the chain extension step is performed before the production step, a chain extender is preferably provided to a portion of an isocyanate group in the aliphatic tertiary isocyanate compound (A). When the chain extension step is performed during the production step, a chain extender is preferably provided to a portion of a terminal isocyanate group of a polycarbodiimide produced by a carbodiimidization reaction of the aliphatic tertiary isocyanate compound (A) and a portion of an isocyanate group in the aliphatic tertiary isocyanate compound (A) before such a reaction. When the chain extension step is performed after polycarbodiimide production, a chain extender is preferably provided to a portion or full of a terminal isocyanate group in a polycarbodiimide compound produced.

The end-capping step may also be performed only at any time point before the carbodiimide production step, during the production step, or after the production step. The chain extension step may also be performed only at any time point before the carbodiimide production step, during the production step, or after the production step.

The method may comprise an adsorption and removal step of performing adsorption and removal of the organic alkali metal compound (B) having Lewis basicity, with an adsorbent (E), after the carbodiimide production step.

No organic phosphorus compound is substantially used, preferably used at all, in the method for producing a carbodiimide compound according to the present embodiment. When no organic phosphorus compound is used, a catalyst removal step performed after carbodiimide production can be omitted, provided that a removal step of any other catalyst may be performed even in no use of any organic phosphorus compound.

Next, each of the steps will be described.

[Carbodiimide Production Step]

The method for producing a carbodiimide compound according to the present embodiment comprises a carbodiimide production step of reacting an aliphatic tertiary isocyanate compound (A) in the presence of an organic alkali metal compound (B) having Lewis basicity.

<Aliphatic Tertiary Isocyanate Compound (A)>

The aliphatic tertiary isocyanate compound (A) in the present embodiment refers to an isocyanate compound in which an isocyanate group is directly bonded to a carbon atom other than those on an aromatic ring and such a carbon atom to which the isocyanate group is directly bonded is a tertiary carbon atom.

For example, a compound in which an isocyanate group is directly bonded to a tertiary carbon atom of a hydrocarbon forming a chain structure, and a compound in which an isocyanate group is directly bonded to a tertiary carbon atom forming an alicyclic structure each correspond to the aliphatic tertiary isocyanate compound (A). A compound in which, even if an aromatic ring is in its molecule, an isocyanate group is directly bonded not to the aromatic ring, but to a tertiary carbon atom other than those on the aromatic ring, also corresponds to the aliphatic tertiary isocyanate compound (A).

The aliphatic tertiary isocyanate compound (A) may be any of a monoisocyanate compound, a diisocyanate compound, and an isocyanate compound in which three or more isocyanate groups are present in one molecule.

A compound, in which two or more isocyanate groups are present in one molecule, corresponds to the aliphatic tertiary isocyanate compound (A) as long as at least one isocyanate group is directly bonded to a tertiary carbon atom other than those on an aromatic ring. Herein, all such isocyanate groups in one molecule are each preferably directly bonded to a tertiary carbon atom other than those on an aromatic ring.

A hydrocarbon moiety except for an isocyanate group in the aliphatic tertiary isocyanate compound (A) may or may not have a substituent other than a hydrocarbon group, preferably has no substituent other than a hydrocarbon group.

The aliphatic tertiary isocyanate compound (A) may or may not have a chain structure, may or may not have an alicyclic structure, and may or may not have an aromatic ring.

The aliphatic tertiary isocyanate compound (A) is preferably a compound in which at least one aromatic ring is bonded to a tertiary carbon atom to which an isocyanate group is bonded. Although the reason is not clear, it is considered that, when such an aromatic ring is bonded, an intermediate made by attacking an isocyanate group by the organic alkali metal (B) having Lewis basicity is stabilized in generation of such an intermediate and thus carbodiimidization easily progresses.

When a plurality of tertiary carbon atoms each bonded to an isocyanate group are present in one molecule, at least one aromatic ring may be bonded to at least one of such tertiary carbon atoms. When a plurality of tertiary carbon atoms each bonded to an isocyanate group are present in one molecule, however, at least one aromatic ring is preferably bonded to each of all such tertiary carbon atoms.

The aliphatic tertiary isocyanate compound (A) is preferably a compound represented by the following general formula (3):

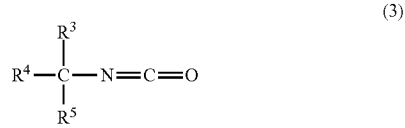

(3)

wherein $R^3$ to $R^5$ are each independently a monovalent residue of any organic compound (provided that a carbon atom in each of $R^3$ to $R^5$ is independently bonded to a carbon atom in the formula (3)), preferably a substituted or unsubstituted hydrocarbon group, for example, a substituted or unsubstituted alkyl group, alkenyl group or aromatic group, for example, an alkyl group or aromatic group not substituted with any group other than an isocyanate group, namely, an alkyl group substituted or unsubstituted with an isocyanate group, or an aromatic group substituted or unsubstituted with an isocyanate group.

$R^3$ to $R^5$ may each independently have one or more isocyanate groups. Alternatively, one of $R^3$ to $R^5$ may have one or more isocyanate groups, or $R^3$ to $R^5$ may have no isocyanate group.

$R^3$ to $R^5$ are not particularly limited, and may each independently have, for example, 1 to 20 carbon atoms, for example, 1 to 10 carbon atoms, or more carbon atoms.

At least one of $R^3$ to $R^5$ is preferably a substituted or unsubstituted aromatic group. Although the reason is not clear, it is considered that, when such a substituted or unsubstituted aromatic group is adopted, an intermediate made by attacking an isocyanate group by the organic alkali metal (B) having Lewis basicity is stabilized in generation of such an intermediate and thus carbodiimidization easily progresses.

The substituted or unsubstituted aromatic group is preferably a substituted or unsubstituted aryl group having 6 to 20 carbon atoms, more preferably a substituted or unsubstituted phenyl group. The substituent in the substituted or unsubstituted aromatic group is preferably an alkyl group having 1 to 20 carbon atoms or an alkenyl group having 2 to 20 carbon atoms, more preferably an alkyl group having 1 to 4 carbon atoms or an alkenyl group having 2 to 4 carbon atoms.

Examples of the compound represented by the general formula (3) include monoisocyanates such as 3-isopropenyl-α,α-dimethylbenzyl isocyanate (TMI); and diisocyanates such as tetramethylxylylene diisocyanate (TMXDI).

When the aliphatic tertiary isocyanate compound (A) is a compound in which an isocyanate group is directly bonded to a tertiary carbon atom of a hydrocarbon forming an alicyclic structure, examples of the alicyclic structure include an adamantane structure, a norbornane structure, a norbornadiene structure, a bicycloundecane structure, a decahydronaphthalene structure, a cubane structure, a basketane structure, and a housane structure. A substituent other than an isocyanate group may or may not be bonded to the alicyclic structure.

The aliphatic tertiary isocyanate compound (A) is preferably at least one of tetramethylxylylene diisocyanate (TMXDI) and 3-isopropenyl-α,α-dimethylbenzyl isocyanate (TMI), more preferably TMXDI or TMI, further preferably TMXDI.

When the aliphatic tertiary isocyanate compound (A) is a monoisocyanate compound, the method for producing a carbodiimide compound according to the present embodiment enables a decarboxylation condensation reaction of isocyanate groups of two such monoisocyanate compounds to occur, thereby producing a monocarbodiimide compound.

When the aliphatic tertiary isocyanate compound (A) is a polyisocyanate compound, the method for producing a carbodiimide compound according to the present embodiment not only enables two such polyisocyanate compounds to be polymerized, thereby producing a monocarbodiimide compound, but also enables three or more such polyisocyanate compounds to be polymerized, thereby producing a polycarbodiimide compound.

The monoisocyanate compound means a compound having one isocyanate group. The polyisocyanate compound means a compound having two or more isocyanate groups. The term "isocyanate compound" conceptually encompasses the monoisocyanate compound and the polyisocyanate compound.

The monocarbodiimide compound means a compound having one carbodiimide group. The polycarbodiimide compound means a compound having two or more carbodiimide groups. The term "carbodiimide compound" conceptually encompasses the monocarbodiimide compound and the polycarbodiimide compound.

A polymerization degree of the carbodiimide compound, of P, in the present embodiment means that, when a carbodiimide compound is produced by subjecting such an isocyanate compound to a decarboxylation condensation reaction, the number of carbodiimide group(s) generated in one molecule of the carbodiimide compound is P. For example, when P+1 diisocyanate compounds are polymerized to produce a polycarbodiimide compound having P carbodiimide group(s), the polymerization degree of the resulting carbodiimide compound is P. Even when P−1 diisocyanate compound(s) and two such monoisocyanate compounds are polymerized to produce an end-capped polycarbodiimide compound having P carbodiimide group(s), the polymerization degree of the resulting carbodiimide compound is P.

The NCO % in a carbodiimide compound generated by a carbodiimidization reaction of the aliphatic tertiary isocyanate compound (A) in the present embodiment means the content (% by mass) of an isocyanate group (NCO group) in the resulting carbodiimide compound. The NCO % can be determined by a method described in Examples.

<Organic Alkali Metal Compound (B) Having Lewis Basicity>

The carbodiimidization catalyst for use in the present embodiment is an organic alkali metal compound (B) having Lewis basicity. The organic alkali metal compound (B) having Lewis basicity for use in the present embodiment contains no phosphorus atom in its molecule. Thus, there are avoided the problems of the remaining organic phosphorus compound in the resulting carbodiimide compound, which interferes with an object material to result in difficulty of use in use of the resultant as an additive, and of the occurrence of any labor hour for removal of the remaining organic phosphorus compound.

The amount of the organic alkali metal compound (B) having Lewis basicity, to be added, based on 100 parts by mass of the aliphatic tertiary isocyanate compound (A) may be 0.01 parts by mass or more and is preferably 0.01 parts by mass or more and 5 parts by mass or less, although the upper limit thereof is not particularly set. An amount of 0.01 parts by mass or more allows the promotion effect of a carbodiimide reaction to be excellent, and an amount of more than 5 parts by mass does not allow the promotion effect of a carbodiimide reaction to be sufficiently enhanced even by further addition. The amount to be added is more preferably 0.05 to 3 parts by mass and further preferably 0.1 to 1 part by mass from such a viewpoint.

The organic alkali metal compound (B) having Lewis basicity is preferably at least one of a metal alkoxide, a metal amide, and a metal carboxylate, and, in one aspect, is a metal amide.

<<Metal Alkoxide>>

The metal alkoxide is an alkali metal alkoxide.

The alkali metal alkoxide is preferably a compound represented by the following general formula (5):

$$M\text{-}OR^{10} \qquad (5)$$

wherein M is an alkali metal, preferably at least one of lithium (Li), sodium (Na), potassium (K), rubidium (Rb), cesium (Cs), and francium (Fr), more preferably at least one of lithium (Li), sodium (Na), cesium (Cs), and potassium (K), and further preferably at least one lithium (Li), sodium (Na), and potassium (K); and wherein $R^{10}$ is preferably an alkyl group having 1 to 20 carbon atoms or an aryl group having 6 to 20 carbon atoms, more preferably an alkyl group having 1 to 20 carbon atoms, further preferably an alkyl group having 1 to 10 carbon atoms, still further preferably an alkyl group having 1 to 6 carbon atoms, still further preferably an alkyl group having 1 to 4 carbon atoms, still further preferably an alkyl group having 2 to 4 carbon atoms, and still further preferably at least one of an ethyl group and a tert-butyl group.

The alkali metal alkoxide is preferably at least one of potassium tert-butoxide, sodium tert-butoxide, potassium ethoxide, and sodium ethoxide, and more preferably at least one of potassium tert-butoxide and sodium ethoxide.

<<Metal Amide>>

The metal amide is preferably an alkali metal amide such as lithium amide, sodium amide, potassium amide, or cesium amide, more preferably lithium amide, and further preferably lithium diisopropyl amide (LDA).

<<Metal Carboxylate>>

The metal carboxylate is preferably an alkali metal acetate, more preferably at least one of potassium acetate and cesium acetate.

A suitable type of an organic compound bonded to an alkali metal in the organic alkali metal compound (B) having Lewis basicity is different depending on the type of the alkali metal.

That is, when the alkali metal is lithium, sodium, or potassium, the organic alkali metal compound (B) having Lewis basicity is preferably at least one of a metal alkoxide, a metal amide, and a metal carboxylate, and more preferably at least one of a metal alkoxide and a metal amide, from the viewpoints of handleability and stability.

When the alkali metal is cesium, the organic alkali metal compound (B) having Lewis basicity is preferably at least one of cesium alkoxide, cesium amide, and cesium carboxylate, and more preferably cesium carboxylate, from the viewpoints of handleability and stability.

<Phase Transfer Catalyst (C)>

The aliphatic tertiary isocyanate compound (A) may be reacted in the presence of the organic alkali metal compound (B) having Lewis basicity and a phase transfer catalyst (C) in the carbodiimide production step. Thus, the carbodiimide compound can be more rapidly obtained.

The "phase transfer catalyst" in the present embodiment refers to a reagent for use in a reaction of an organic compound insoluble in water and a compound insoluble in an organic solvent, particularly refers to a reagent for use in an efficient reaction of such a tertiary isocyanate group-containing compound (A) and the organic alkali metal compound (B) having Lewis basicity.

The amount of the phase transfer catalyst (C) to be added may be 0.01 parts by mass or more based on 100 parts by mass of the aliphatic tertiary isocyanate compound (A), and the upper limit thereof is not particularly set. An amount of 0.01 parts by mass or more allows the promotion effect of a carbodiimide reaction to be excellent, and an amount of 300 parts by mass or more does not allow the promotion effect of a carbodiimide reaction to be sufficiently enhanced even by further addition. The amount to be added is more preferably 0.01 to 300, further preferably 0.05 to 200 parts by mass, and still further preferably 0.1 to 100 parts by mass, from such a viewpoint. When the amount of the phase transfer catalyst (C) to be added is decreased, the effect can be exerted even in the case of an amount of 10 parts by mass or less, for example, 5 parts by mass or less.

The phase transfer catalyst (C) for use in the present embodiment is not particularly limited, and is preferably at least one of crown ether, a quaternary ammonium salt, and polyalkylene glycol dialkyl ether, more preferably at least one crown ether, a quaternary ammonium salt, and a compound represented by general formula (1), described below.

Among these, crown ether is more preferable from the viewpoint of an enhancement in reaction rate, and at least one of a quaternary ammonium salt and a polyalkylene glycol dialkyl ether is more preferable from the viewpoint of economic efficiency.

<<Crown Ether>>

The crown ether is not particularly limited, and may be any narrowly defined crown ether represented by general structure formula  (n is an integer), may be any thiacrown ether in which some or all oxygen atoms forming a crown ether ring are each substituted with a sulfur atom, or may be any azacrown ether in which some or all the oxygen atoms are each substituted with NR (R is a substituent) or the like. Such crown ether may be modified. For example, any narrowly defined crown ether not modified may also be used.

The crown ether is preferably at least one of 4'-acetyl-benzo-15-crown 5-ether, 4'-acetylbenzo-18-crown 6-ether, 4'-aminobenzo-15-crown 5-ether, 1-aza-12-crown 4-ether, 1-aza-15-crown 5-ether, 1-aza-18-crown 6-ether, benzo-12-crown 4-ether, benzo-15-crown 5-ether, benzo-18-crown 6-ether, bis(1,4-phenylene)-34-crown 10-ether, 4'-bromobenzo-15-crown 5-ether, 4'-bromobenzo-18-crown 6-ether, 4'-carboxybenzo-15-crown 5-ether, 4'-carboxybenzo-18-crown 6-ether, 15-crown 4[4-(2,4-dinitrophenylazo)phenol], 18-crown 5[4-(2,4-dinitrophenylazo)phenol], 12-crown 4-ether, 15-crown 5-ether, 18-crown 6-ether, 24-crown 8-ether, 4,10-diaza-12-crown 4-ether, 4,10-diaza-15-crown 5-ether, 4,13-diaza-18-crown 6-ether, dibenzo-15-crown 5-ether, dibenzo-18-crown 6-ether, dibenzo-21- crown 7-ether, dibenzo-24-crown 8-ether, dibenzo-30-crown 10-ether, N,N'-dibenzyl-4,13-diaza-18-crown 6-ether, dicyclohexano-18-crown 6-ether, 4'-formylbenzo-15-crown 5-ether, 4'-formylbenzo-18-crown 6-ether, 1,4,7,10,13,16-hexaazacyclooctadecane, 1,4,7,10,13,16-hexaazacyclooctadecanehexahydrochloride, 4,7,13,16,21,24-hexaoxa-1,10-diazabicyclo[8.8.8]hexacosane, 2-(hydroxymethyl)-12-crown 4-ether, 2-(hydroxymethyl)-15-crown 5-ether, 2-(hydroxymethyl)-18-crown 6-ether, 4'-methoxycarbonylbenzo-15-crown 5-ether, 4'-nitrobenzo-15-crown 5-ether, 4'-nitrobenzo-18-crown 6-ether, N-phenylaza-15-crown 5-ether, 1,4,7,10-tetraazacyclododecane, 1,4,7,10-tetraazacyclododecane-1,4,7,10-tetraacetic acid, 1,4,7,10-tetraazacyclododecane tetrahydrochloride, 1,4,8,12-tetraazacyclopentadecane, 1,4,8,11-tetraazacyclotetradecane, 1,4,7,10-tetrabenzyl-1,4,7,10-tetraazacyclododecane, tetraethyl-1,4,8,11-tetraazacyclotetradecane-1,4,8,11-tetraacetate, 1,4,8,11-tetramethyl-1,4,8,11-tetraazacyclotetradecane, 1,4,8,11-tetrathiacyclotetradecane, 1,5,9-triazacyclododecane, 1,4,7-triazacyclononane, 1,4,7-triazacyclononane trihydrochloride, tri-tert-butyl-1,4,7,10-tetraazacyclododecane-1,4,7,10-tetraacetate, tri-tert-butyl-1,4,7,10-tetraazacyclododecane-1,4,7-triacetate, 1,4,7-trimethyl-1,4,7-triazacyclononane (stabilized with NaHCO$_3$), and 1,4,7-trithiacyclononane.

Among these, at least one of 12-crown 4-ether, 15-crown 5-ether, 18-crown 6-ether, and 24-crown 8-ether is more preferable, and 18-crown 6-ether and/or 15-crown 5-ether are/is further preferable.

The crown ether is preferably appropriately selected depending on the type of the cation in the organic alkali metal compound (B) having Lewis basicity. For example, 18-crown 6-ether is preferable when the cation is potassium (K), and 15-crown 5-ether is preferable when the cation is sodium (Na).

<<Quaternary Ammonium Salt>>

The quaternary ammonium salt is not particularly limited, and is preferably at least one of tetrabutylammonium bromide, tetrabutylammonium iodide, tetrabutylammonium-2-ethylhexanoate, tetrabutylammonium hydrogen sulphate, tetrabutylammonium chloride, tetrabutylammonium fluoride trihydrate, tetrabutylaminium nitrate (Tetrabutylammonium nitrate), tetrabutylaminium nitrite (Tetrabutylammonium nitrite), tetrabutylammonium acetate, tetrabutylammonium triiodide, tetraethylammonium bromide, tetraethylammonium chloride, tetraethylammonium fluoride dihydrate, tetrapropylammonium bromide, tetrapropylammonium chloride, tetramethylammonium chloride, benzyltriethylammonium chloride, benzyltriethylammonium bromide, benzyltrimethylammonium chloride, benzyltrimethylammonium bromide, benzyltrimethylammonium dichloroiodate, benzyltributylammonium chloride, benzyltributylammonium bromide, methyltributylammonium chloride, methyltributylammonium bromide, methyltriethylammonium chloride, methyltriethylammonium bromide, phenyltrimethylammonium chloride, behentrimonium chloride, cetyltrimethylammonium bromide, cetyltrimethylammonium chloride, cetyltrimethylammonium hydrogen sulphate, cetalkonium chloride, cetalkonium bromide, cetyldimethylbenzylammonium chloride, cetyldimethylethylammonium bromide, cetrimide, didecyldimethylammonium chloride, dodecyltrimethylammonium chloride, dodecyltrimethylammonium bromide, myristyltrimethylammonium bromide, methyltrioctylammonium chloride, tetra-n-octylammonium bromide, trimethyl-n-octylammonium bromide, and trioctyl methyl ammonium bromide.

Among these, a tetrabutylammonium salt, for example, tetrabutylammonium-2-ethylhexanoate is preferable from the viewpoint of availability.

<<Polyalkylene Glycol Dialkyl Ether>>

The polyalkylene glycol dialkyl ether is not particularly limited, and is preferably a compound represented by the following general formula (1);

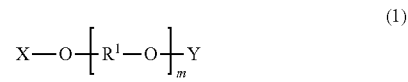

(1)

wherein X and Y are each independently a methyl group, an ethyl group, a propyl group, a butyl group, or a phenyl group; $R^1$ is an alkylene group having 2 to 3 carbon atoms; and m is an integer of 2 to 500, preferably an integer of 3 to 300, and more preferably an integer of 4 to 200.

The compound represented by the formula (1) is preferably at least one of polyoxyethylene dialkyl ether and polyoxypropylene dialkyl ether.

The polyoxyethylene dialkyl ether is preferably at least one of polyoxyethylene dimethyl ether, polyoxyethylene diethyl ether, polyoxyethylene dipropyl ether, polyoxyethylene dibutyl ether, and polyoxyethylene diphenyl ether.

The polyoxypropylene dialkyl ether is preferably at least one of polyoxypropylene dimethyl ether, polyoxypropylene diethyl ether, polyoxypropylene dipropyl ether, polyoxypropylene dibutyl ether, and polyoxypropylene diphenyl ether.

The number average molecular weight of the polyalkylene glycol dialkyl ether is preferably 100 or more from the viewpoint of an enhancement in reaction rate of a carbodiimidization reaction of the tertiary isocyanate group-containing compound (A), and is preferably 5000 or less from the viewpoints of handleability and solubility. The number average molecular weight is more preferably 100 to 1000, further preferably 100 to 800, still further preferably 200 to 700, still further preferably 250 to 700, and still further preferably 300 to 600 from the same viewpoints.

<Other Component>

Any component other than the above may be added in the carbodiimide production step.

For example, an organic solvent may be added. The organic solvent is preferably an organic solvent having no active hydrogen group and having a higher boiling point than the temperature in synthesis, for example, ethylene glycol monomethyl ether acetate (118.13), diethylene glycol dimethyl ether (134.18), dipropylene glycol dimethyl ether (162.23), diethylene glycol ethyl methyl ether (148.20), diethylene glycol isopropyl methyl ether (162.23), diethylene glycol diethyl ether (162.23), diethylene glycol butyl methyl ether (176.26), tripropylene glycol dimethyl ether (206.28), triethylene glycol dimethyl ether (178.23), diethylene glycol dibutyl ether (218.34), triethylene glycol butyl methyl ether (220.31), or tetraethylene glycol dimethyl ether (222.28). Thus, the reaction rate of the carbodiimidization reaction may be enhanced and/or the resulting polycarbodiimide is easily adjusted in terms of the viscosity thereof. Each number in parentheses represents each molecular weight.

The amount of such other component to be added is preferably 200 parts by mass or less, more preferably 100 parts by mass or less, and further preferably 10 parts by mass or less based on 100 parts by mass of the tertiary isocyanate group-containing compound (A).

<Reaction Conditions>

The reaction temperature in the carbodiimide production step is appropriately set depending on the type of the aliphatic tertiary isocyanate compound (A).

The reaction temperature is preferably 50° C. or more, more preferably 80° C. or more, and further preferably 100° C. or more, and, when the decomposition temperature of the aliphatic tertiary isocyanate compound (A) is X° C., the reaction temperature is preferably X° C. or less, more preferably X–5° C. or less, and further preferably X–10° C. or less.

For example, when the aliphatic tertiary isocyanate compound (A) is at least one of tetramethylxylylene diisocyanate and 3-isopropenyl-α,α-dimethylbenzyl isocyanate, the reaction temperature is preferably 80 to 200° C., more preferably 100 to 190° C., and further preferably 130 to 180° C.

The reaction atmosphere is preferably an atmosphere of an inert gas such as a nitrogen gas. The method for inclusion of the inert gas may be in a flowing manner or in a bubbling manner for inclusion into a liquid.

[End-Capping Step]

The method for producing carbodiimide in the present embodiment may comprise an end-capping step of reacting a portion of an isocyanate group in the aliphatic tertiary isocyanate compound (A) with an end-capping agent, at at least one time point among three time points, before the carbodiimide production step, during the production step, and after the production step.

The end-capping step enables the polymerization degree of the resulting carbodiimide compound to be controlled.

The end-capping agent may be any organic compound having a functional group reactive with a terminal isocyanate group of the carbodiimide compound. Examples of the organic compound having a functional group reactive with such an isocyanate group include a compound having active hydrogen, such as alcohol, amine, and carboxylic acid, a compound having a monoisocyanate group, and a compound (D-1) represented by general formula (2-1), described below, and a compound (D-1) represented by general formula (2-1), described below, is preferable.

The end-capping step may be performed at at least one time point among three time points, before the carbodiimide production step, during the production step, and after the production step, may be performed at only any one time point, or may be performed, for example, before the production step.

The aliphatic tertiary isocyanate compound (A) is partially end-capped with the end-capping agent in the end-capping step. Such an aliphatic tertiary isocyanate compound (A) partially end-capped can be thus subjected to the carbodiimide production step, thereby producing a carbodiimide compound which is end-capped. Furthermore, the polymerization degree of the resulting carbodiimide compound can be controlled. It is noted that the aliphatic tertiary isocyanate compound (A) here used may be an aliphatic tertiary isocyanate compound (A) in which an isocyanate group is partially end-capped in advance, and the end-capping step may be omitted.

<Compound (D-1) Represented by General Formula (2-1)>

The compound (D-1) for use in the present embodiment is represented by the following general formula (2-1);

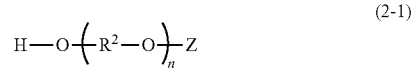

(2-1)

wherein Z is a methyl group, an ethyl group, a propyl group, a butyl group, or a phenyl group; $R^2$ is an alkylene group having 2 to 3 carbon atoms; and n is an integer of 2 to 500, preferably an integer of 3 to 300, and more preferably an integer of 4 to 200.

The compound (D-1) represented by the formula (2-1) is preferably at least one of polyoxyethylene monoalkyl ether and polyoxypropylene monoalkyl ether.

The polyoxyethylene monoalkyl ether is preferably at least one of polyoxyethylene monomethyl ether, polyoxyethylene monoethyl ether, polyoxyethylene monopropyl ether, polyoxyethylene monobutyl ether, and polyoxyethylene monophenyl ether.

The polyoxypropylene monoalkyl ether is preferably at least one of polyoxypropylene monomethyl ether, polyoxypropylene monoethyl ether, polyoxypropylene monopropyl ether, polyoxypropylene monobutyl ether, and polyoxypropylene monophenyl ether.

The compound (D-1) is used as the end-capping agent, thereby partially end-capping the aliphatic tertiary isocyanate compound (A) due to a urethanization reaction of a portion of an isocyanate group in the aliphatic tertiary isocyanate compound (A) with a hydroxyl group of the compound (D-1). Thus, the aliphatic tertiary isocyanate compound (A) is partially end-capped with the compound (D-1) and then subjected to the carbodiimide production step, and thus is enhanced in reaction rate of the carbodiimidization reaction because a residue of the compound (D-1) acts in the same manner as in the phase transfer catalyst.

Such end-capping of the aliphatic tertiary isocyanate compound (A) with the compound (D-1) can be performed at at least one time point among three time points, before the above-mentioned carbodiimide production step, during the production step, and after the production step, and is preferably performed before the production step.

The number average molecular weight of the compound (D-1) is preferably 100 or more from the viewpoint of an enhancement in reaction rate of the carbodiimidization reaction of the tertiary isocyanate group-containing compound (A), and is preferably 5000 or less from the viewpoints of handleability and solubility. The number average molecular weight is more preferably 100 to 1000, further preferably 100 to 800, still further preferably 200 to 700, still further preferably 250 to 700, and still further preferably 300 to 600 from the same viewpoints.

The amount of the compound (D-1) to be added can be appropriately selected depending on the polymerization degree of a carbodiimide compound to be produced.

The amount of the compound (D-1) to be added is here preferably 0.01 parts by mass or more, more preferably 0.1 parts by mass or more, and further preferably 1.0 parts by mass or more based on 100 parts by mass of the aliphatic tertiary isocyanate compound (A), from the viewpoint of promotion of the carbodiimide reaction. The amount of the compound (D-1) to be added is preferably 200 parts by mass or less, more preferably 50 parts by mass or less, and further preferably 5.0 parts by mass or less based on 100 parts by mass of the aliphatic tertiary isocyanate compound (A) from an economic viewpoint and from the viewpoint of securement of the concentration of carbodiimide.

<Reaction Conditions>

The reaction temperature in the end-capping step is appropriately set depending on the type of the aliphatic tertiary isocyanate compound (A).

The reaction temperature is preferably 50° C. or more, more preferably 80° C. or more, further preferably 100° C. or more, and, when the decomposition temperature of the aliphatic tertiary isocyanate compound (A) is X° C., the reaction temperature is preferably X° C. or less, more preferably X−5° C. or less, and further preferably X−10° C. or less.

A urethanization catalyst may be, if necessary, used to allow the reaction to occur at a lower temperature.

For example, when the aliphatic tertiary isocyanate compound (A) is at least one of tetramethylxylylene diisocyanate and 3-isopropenyl-α,α-dimethylbenzyl isocyanate, the reaction temperature is preferably 80 to 200° C., more preferably 100 to 190° C., and further preferably 130 to 180° C.

The reaction atmosphere is preferably an atmosphere of an inert gas such as a nitrogen gas. The method for inclusion of the inert gas may be in a flowing manner or in a bubbling manner for inclusion into a liquid.

[Chain Extension Step]

The method for producing carbodiimide in the present embodiment may comprise a chain extension step of reacting a portion of an isocyanate group in a carbodiimide compound obtained by the reaction of the aliphatic tertiary isocyanate compound (A) with a chain extender, at at least one time point among three time points, before the carbodiimide production step, during the production step, and after the production step, provided that the chain extension step is not necessarily performed.

The chain extender may be any organic compound having two or more functional groups each reactive with a terminal isocyanate group of the carbodiimide compound. The organic compound is preferably a polyol having two or more hydroxyl groups or a polyamine having two or more amino groups, more preferably diol or diamine, and further preferably a compound (D-2) represented by general formula (2-2), described below.

The chain extension step may be performed at at least one time point among three time points, before the carbodiimide production step, during the production step, and after the production step, may be performed at only any one time point, or may be performed, for example, after the production step.

The chain extension step enables the polymerization degree of the resulting carbodiimide compound to be controlled, provided that the chain extension step may be omitted.

<Compound (D-2) Represented by General Formula (2-2)>

The compound (D-2) for use in the present embodiment is represented by the following general formula (2-2);

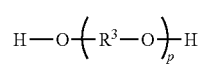

$$H-O+R^3-O+_pH \quad (2-2)$$

wherein $R^3$ is an alkylene group having 2 to 3 carbon atoms; and p is an integer of 2 to 500.

The compound (D-2) is used as the chain extender, thereby resulting in chain extension of a portion of an end of the aliphatic tertiary isocyanate compound (A) due to a urethanization reaction of a portion of an isocyanate group in the aliphatic tertiary isocyanate compound (A) with a hydroxyl group of such a chain extender (D-2). Such an aliphatic tertiary isocyanate compound containing a substituent, whose end is thus partially subjected to chain extension with the chain extender (D-2), is enhanced in reaction rate of the carbodiimidization reaction because a residue of the compound (D-2) to serves as the phase transfer catalyst.

The compound (D-2) is preferably at least one of polyoxyethylene and polyoxypropylene.

Such chain extension with the compound (D-2) may be performed at at least one time point among three time points, before the above-mentioned carbodiimide production step, during the production step, and after the production step, may be performed at only any one time point, or may be performed, for example, after the production step.

The number average molecular weight of the compound (D-2) is preferably 100 or more from the viewpoint of an enhancement in reaction rate of the carbodiimidization reaction of the tertiary isocyanate group-containing compound (A), and is preferably 5000 or less from the viewpoints of handleability and solubility. The number average molecular weight is more preferably 100 to 1000, further preferably 100 to 800, still further preferably 200 to 700, still further preferably 250 to 700, and still further preferably 300 to 600 from the same viewpoints.

The amount of compound (D-2) to be added can be appropriately selected depending on the polymerization degree of a carbodiimide compound to be produced.

When the compound (D-2) is here added, the amount thereof to be added is preferably 0.01 parts by mass or more, more preferably 0.1 parts by mass or more, and further preferably 1.0 parts by mass or more based on 100 parts by mass of the aliphatic tertiary isocyanate compound (A), from the viewpoint of promotion of the carbodiimide reaction. The amount of compound (D-2) to be added is preferably 200 parts by mass or less, more preferably 50 parts by mass or less, and further preferably 5.0 parts by mass or less based on 100 parts by mass of the aliphatic tertiary isocyanate compound (A), from an economic viewpoint and from the viewpoint of securement of the concentration of carbodiimide.

<Reaction Conditions>

The reaction temperature in the chain extension step is appropriately set depending on the type of the aliphatic tertiary isocyanate compound (A). The detail of the reaction conditions is the same as in the case of the end-capping step.

[Adsorption and Removal Step]

The method for producing carbodiimide in the present embodiment may comprise an adsorption and removal step of performing adsorption and removal of the organic alkali metal compound (B) having Lewis basicity, with an adsorbent (E), during or after the carbodiimide production step, preferably after the carbodiimide production step. Thus, the organic alkali metal compound (B) having Lewis basicity can be sufficiently removed from the resulting carbodiimide compound, provided that the adsorption and removal step may be omitted.

The organic alkali metal compound (B), when used in combination with an antioxidant, may cause coloration, and thus the content of the organic alkali metal compound (B) in the carbodiimide compound is preferably 2000 ppm by mass or less, more preferably 1000 ppm by mass or less, and further preferably 200 ppm by mass or less.

An adsorption procedure may be any of a stirring and admixing method involving admixing an adsorbent into the carbodiimide compound and then performing filtration, and a filtration layer method involving allowing the carbodiimide compound to be distributed in a filtration layer filled with an adsorbent, and such an adsorbent may be subjected to no filtration after admixing thereof with the carbodiimide compound.

<Adsorbent (E)>

The adsorbent (E) for use in the present embodiment is not particularly limited, and is preferably at least one of a synthetic aluminum silicate-based adsorbent, synthetic magnesium silicate, an acidic cation-exchange resin, a basic anion-exchange resin, alumina, a silica gel-based adsorbent, a zeolite-based adsorbent, hydrotalcites, a magnesium oxide-aluminum oxide-based solid solution, aluminum hydroxide, magnesium oxide, and an aluminum hydroxide-sodium hydrogen carbonate coprecipitate (dawsonite), and more preferably at least one of a synthetic aluminum silicate-based adsorbent, a synthetic magnesium silicate-based adsorbent, an acidic cation-exchange resin, a basic anion-exchange resin, alumina, a silica gel-based adsorbent, and a zeolite-based adsorbent.

The amount of the adsorbent (E) to be added is preferably 50 to 5000 parts by mass, more preferably 100 to 1000 parts by mass, further preferably 200 to 1000 parts by mass, and further preferably 400 to 800 parts by mass based on 100 parts by mass of the organic alkali metal compound (B) having Lewis basicity.

<Carbodiimide Compound>

The method for producing a carbodiimide compound according to the present embodiment enables a carbodiimide compound to be produced by a reaction of an aliphatic tertiary isocyanate compound, at a high yield, even in the case of substantial no use of any organic phosphorus compound as a carbodiimidization catalyst.

The carbodiimide compound obtained by the method for producing a carbodiimide compound according to the present embodiment preferably has a purity (content) of 90% by mass or more, and comprises no phospholene oxides or comprises phospholene oxides at a content of 1 ppm by mass or less.

The purity (content) here means the content of the carbodiimide compound in an active component of a product obtained by the method for producing a carbodiimide compound according to the present embodiment. The active component here means the total amount of component(s) except for a solvent when the product comprises the solvent, and means the total amount of the product when the product comprises no solvent. Much the same is true on a stabilizer and a carbodiimide composition described below.

A carbodiimide compound according to the present embodiment can be suitably used for preventing hydrolysis of a resin. Examples of the resin here include a thermoplastic polyurethane, and such a resin can be added to a diisocyanate as a raw material of a urethane resin in advance, and stored, and can be used for production of a urethane resin comprising a stabilizer through no step of adding such a stabilizer after production of such a urethane resin.

2. Stabilizer

A stabilizer according to the present embodiment is a stabilizer comprising a carbodiimide compound with an aliphatic tertiary isocyanate compound (A) as a structural unit, and an alkali metal (alkali metal derived from an organic alkali metal compound (B) having Lewis basicity), and comprising no phospholene oxides or comprising phospholene oxides at a content of 1 ppm by mass or less.

The stabilizer is useful as a stabilizer for various resins such as a thermoplastic resin, or useful for inhibition of hydrolysis. The stabilizer can be added to any diisocyanate as a raw material of a urethane resin in advance, and stored, and is useful for production of a urethane resin comprising the stabilizer through no step of adding the stabilizer to the urethane resin. The resin is not particularly limited, and examples thereof include polyurethane and thermoplastic polyurethane.

The aliphatic tertiary isocyanate compound (A) as a structural unit of the carbodiimide compound comprised in the stabilizer is suitably the same as that used in "1. Method for producing carbodiimide compound" described above.

The carbodiimide compound may be end-capped with an end-capping agent as described in "1. Method for producing carbodiimide compound". The end-capping agent is suitably the above-mentioned compound (D-1).

The carbodiimide compound may be capped with a chain extender, as described in "1. Method for producing carbodiimide compound". The chain extender is suitably the above-mentioned compound (D-2).

The content (namely, purity) of the carbodiimide compound with the aliphatic tertiary isocyanate compound (A) as a structural unit in the stabilizer is preferably 80% by mass or more, more preferably 90% by mass or more, further preferably 95% by mass or more, and still further preferably 99% by mass.

The alkali metal comprised in the stabilizer is preferably at least one of lithium (Li), sodium (Na), potassium (K), rubidium (Rb), cesium (Cs), and francium (Fr), more preferably at least one of lithium (Li), sodium (Na), cesium (Cs), and potassium (K), and further preferably at least one lithium (Li), sodium (Na), and potassium (K).

The content of the alkali metal in the stabilizer is preferably less than 2000 ppm by mass. A content of less than 2000 ppm by mass prevents the problem of difficulty of use due to interference with an object material.

The content of the alkali metal in the stabilizer is preferably 10 ppm by mass or more and more preferably 100 ppm by mass or more from the viewpoint of ease of production.

The stabilizer preferably comprises no phospholene oxides or comprises phospholene oxides at a content of 1 ppm by mass or less.

Therefore, the problem of difficulty of use due to interference of phospholene oxides with an object material is prevented.

The stabilizer may further comprise the phase transfer catalyst (C).

The content of the phase transfer catalyst (C) in the stabilizer is preferably 0.1 to 10 parts by mass, more preferably 0.3 to 5 parts by mass, and further preferably 0.5 to 2 parts by mass based on 100 parts by mass of the carbodiimide compound. A content of 10 parts by mass or less prevents troubles such as appearance failure due to bleed-out of the phase transfer catalyst and stickiness in use from occurring in use of any of various resins as the stabilizer, and a content of 0.1 parts by mass or more allows an objective reaction promotion effect to be favorable.

The stabilizer is suitably produced by a production method comprising "1. Method for producing carbodiimide compound" described above.

That is, the stabilizer may be produced only by "1. Method for producing carbodiimide compound" described above, or may be produced through other subsequent step such as addition of other additive.

3. Carbodiimide Composition

A carbodiimide composition according to the present embodiment is a carbodiimide composition comprising a carbodiimide compound with an aliphatic tertiary isocyanate compound (A) as a structural unit, and an alkali metal (alkali metal derived from an organic alkali metal compound (B) having Lewis basicity), and comprising no phospholene oxides or comprising phospholene oxides at a content of 1 ppm by mass or less.

Each component in the carbodiimide composition is the same as in the above-mentioned stabilizer.

4. Method for Producing Polyurethane

A method for producing a polyurethane according to the present embodiment is a method for producing a polyurethane, comprising reacting a polyol and a diisocyanate in the presence of a stabilizer to thereby obtain a polyurethane, preferably a thermoplastic polyurethane, wherein the stabilizer comprises an aliphatic tertiary carbodiimide derived from an aliphatic tertiary isocyanate compound and comprises an alkali metal at a content of less than 2000 ppm by mass.

The amount of the aliphatic tertiary carbodiimide derived from an aliphatic tertiary isocyanate compound, to be added, based on the total amount of 100 parts by mass of the polyol and the diisocyanate is preferably 0.1 to 2 parts by mass, more preferably 0.5 to 1 part by mass.

The aliphatic tertiary carbodiimide derived from an aliphatic tertiary isocyanate compound is preferably metered and loaded at a temperature of preferably 20 to 50° C., particularly preferably 25 to 35° C., in the form of a liquid in a continuous or batch manner.

The stabilizer here suitably used is any stabilizer described in "2. Stabilizer".

A method for producing a polyurethane according to another embodiment is a method for producing a polyurethane, comprising reacting a polyol and a diisocyanate in the presence of a stabilizer to thereby obtain a polyurethane, preferably a thermoplastic polyurethane, wherein the stabilizer is a carbodiimide compound produced by the above method for producing a carbodiimide compound according to the present embodiment.

5. Ester-Based Resin Composition

An ester-based resin composition according to the present embodiment is an ester-based resin composition comprising the above-mentioned carbodiimide composition and an ester-based resin.

The content of the carbodiimide composition in the ester-based resin composition is 0.2 to 5.0 parts by mass based on 100 parts by mass of the ester-based resin.

An ester-based resin composition according to another embodiment is an ester-based resin composition comprising the above-mentioned stabilizer and an ester-based resin. The content of the stabilizer in the ester-based resin composition is preferably 0.2 to 5.0 parts by mass based on 100 parts by mass of the ester-based resin.

EXAMPLES

Hereinafter, the present invention will be described with reference to Examples in more detail, but the present invention is not limited thereto.

Respective evaluations in Examples below were performed according to the following methods.

(1) Infrared (IR) Spectrum Measurement

FTIR-8200PC (manufactured by Shimadzu Corporation) was used.

(2) GPC
RI detector: RID-6A (manufactured by Shimadzu Corporation)
Column: KF-806, KF-804L, KF-804L (manufactured by Showa Denko K.K.)
Developing solvent: tetrahydrofuran (THF) 1 ml/min.
The number average molecular weight (Mn) in terms of the polystyrene equivalent was calculated.

(3) NCO %

A HIRANUMA Automatic Titrator COM-900 (manufactured by HIRANUMA SANGYO Co., Ltd.) and a Tit-Station K-900 (manufactured by HIRANUMA SANGYO Co., Ltd.) were used, a dibutylamine/toluene solution having a known concentration was added, and calculation was made by potentiometric titration with an aqueous hydrochloric acid solution.

(4) Confirmation of Presence or Absence of Carbodiimidization Catalyst

After 10 g of diphenylmethane diisocyanate and 1 g of the resulting polycarbodiimide were mixed, and heated with stirring at 100° C. for 1 hour, an absorption peak was confirmed immediately after the mixing and after the mixing and heating, by infrared (IR) spectrum measurement, and the presence or absence of the carbodiimidization catalyst was confirmed by the presence or absence of peaks (at a wavelength of about 1710 $cm^{-1}$ and a wavelength of about 1411 $cm^{-1}$) derived from an isocyanurate compound of the diphenylmethane diisocyanate and the presence or absence of peaks (at a wavelength of about 2138 $cm^{-1}$ and a wavelength of about 2112 $cm^{-1}$) derived from the carbodiimide compound.

(Quantitative Determination of Alkali Metal)

Each alkali metal comprised in the carbodiimide compound and the stabilizer was subjected to quantitative determination by the following operation according to an inductively coupled plasma (ICP) emission spectroscopic analysis method.

After 1.00 g of the carbodiimide compound or the stabilizer and 19.00 g of ultrapure water were mixed and left to still stand for 24 hours, an aqueous mixed solution was filtered with a 0.1-µm membrane filter. The filtrate thus obtained was subjected to elemental analysis with an inductively coupled plasma (ICP) emission spectroscopic analyzer (product name: ICPS-8100, manufactured by Shimadzu Corporation). The content rate of each alkali metal atom in the carbodiimide compound or the stabilizer was determined with a calibration curve of such each alkali metal, based on the difference calculated from the elemental analysis results obtained and the measurement results of only ultrapure water.

Example 1

100 g of tetramethylxylylene diisocyanate and 0.5 g of an organic alkali metal having Lewis basicity (potassium tert-butoxide) as a carbodiimidization catalyst were placed in a 300-ml reaction container with a reflux tube and a stirrer and stirred under a nitrogen gas flow at 175° C. to perform a reaction until the result of NCO % measurement was 3.74%. The synthesis time (time taken for carbodiimidization) was 26 hours.

Herein, the NCO % value being 3.74% corresponded to the content (% by mass) of a NCO group in a carbodiimide compound (having a NCO group on each of both ends) having a polymerization degree of 10 under the assumption of that the carbodiimide compound was produced by decarboxylation condensation of eleven tetramethylxylylene diisocyanates. Such a value of 3.74% was set as a target value, and the above-mentioned reaction was performed until the measurement value of NCO % reached the target value.

The resulting isocyanate-terminated polytetramethylxylylene carbodiimide (average polymerization degree=10) was analyzed, and, as a result, an absorption peak attributed to a carbodiimide group at a wavelength of about 2118 $cm^{-1}$ was confirmed by infrared (IR) spectrum measurement.

The following could not be confirmed: absorption peaks attributed to an isocyanurate as an isocyanate trimer at absorption wavelengths: a wavelength of about 1710 $cm^{-1}$ and a wavelength of about 1411 $cm^{-1}$; absorption peaks attributed to a uretdione as an isocyanate dimer at absorption wavelengths: a wavelength of about 1765 cm$^{-1}$ and a wavelength of about 1410 cm$^{-1}$; and any absorption peak based on other by-product. Furthermore, GPC measurement was performed, and the polystyrene equivalent number average molecular weight was thus 1891.

The presence or absence of the carbodiimidization catalyst (alkali metal) was confirmed, thus absorption peaks attributed to an isocyanurate of the diphenylmethane diisocyanate at absorption wavelengths: a wavelength of about 1710 cm$^{-1}$ and a wavelength of about 1411 cm$^{-1}$; were observed, and it was thus confirmed that the catalyst remained.

Compounding and synthesis conditions of each raw material are shown in Table 1, and the evaluation results are shown in Table 2. Much the same is true on the following Examples and Comparative Examples.

Example 2

100 g of 3-isopropenyl-α,α-dimethylbenzyl isocyanate and 0.5 g of an organic alkali metal having Lewis basicity (potassium tert-butoxide) as a carbodiimidization catalyst were placed in a 300-ml reaction container with a reflux tube and a stirrer and stirred under a nitrogen gas flow at 175° C. to perform a reaction until any absorption of an isocyanate group at a wavelength of 2200 to 2300 cm$^{-1}$ disappeared in infrared (IR) spectrum measurement (NCO % was 0%). The synthesis time was 45 hours. The resulting di(3-isopropenyl-α,α-dimethylbenzyl)monocarbodiimide was analyzed, and, as a result, an absorption peak attributed to a carbodiimide group at a wavelength of about 2118 cm$^{-1}$ was confirmed by infrared (IR) spectrum measurement. The following could not be confirmed: absorption peaks attributed to an isocyanurate at absorption wavelengths: a wavelength of about 1710 cm$^{-1}$ and a wavelength of about 1411 cm$^{-1}$; absorption peaks attributed to a uretdione at absorption wavelengths: a wavelength of about 1765 cm$^{-1}$ and a wavelength of about 1410 cm$^{-1}$; and any absorption peak based on other by-product. Furthermore, GPC measurement was performed, and the polystyrene equivalent number average molecular weight was thus 145.

The presence or absence of the carbodiimidization catalyst (alkali metal) was confirmed, thus absorption peaks attributed to an isocyanurate of the diphenylmethane diisocyanate at absorption wavelengths: a wavelength of about 1710 cm$^{-1}$ and a wavelength of about 1411 cm$^{-1}$; were observed, and it was thus confirmed that the catalyst remained.

Example 3

100 g of tetramethylxylylene diisocyanate and 0.5 g of an organic alkali metal compound having Lewis basicity (sodium ethoxide) as a carbodiimidization catalyst were placed in a 300-ml reaction container with a reflux tube and a stirrer and stirred under a nitrogen gas flow at 175° C. to perform a reaction until the result of NCO % measurement was 3.74%. The synthesis time was 21 hours. The resulting isocyanate-end polytetramethylxylylene carbodiimide (average polymerization degree=10) was analyzed, and as a result, an absorption peak attributed to a carbodiimide group at a wavelength of about 2118 cm$^{-1}$ was confirmed by infrared (IR) spectrum measurement. The following could not be confirmed: absorption peaks attributed to an isocyanurate at absorption wavelengths: a wavelength of about 1710 cm$^{-1}$ and a wavelength of about 1411 cm$^{-1}$; absorption peaks attributed to a uretdione at absorption wavelengths: a wavelength of about 1765 cm$^{-1}$ and a wavelength of about 1410 cm$^{-1}$; and any absorption peak based on other by-product. Furthermore, GPC measurement was performed, and the polystyrene equivalent number average molecular weight was thus 1886.

The presence or absence of the carbodiimidization catalyst (alkali metal) was confirmed, thus absorption peaks attributed to an isocyanurate of the diphenylmethane diisocyanate at absorption wavelengths: a wavelength of about 1710 cm$^{-1}$ and a wavelength of about 1411 cm$^{-1}$; were observed, and it was thus confirmed that the catalyst remained.

Example 4

100 g of tetramethylxylylene diisocyanate and 0.5 g of an organic alkali metal having Lewis basicity (lithium diisopropylamide) as a carbodiimidization catalyst were placed in a 300-ml reaction container with a reflux tube and a stirrer and stirred under a nitrogen gas flow at 175° C. to perform a reaction until the result of NCO % measurement was 3.74%. The synthesis time was 10 hours. The resulting isocyanate-terminated polytetramethylxylylene carbodiimide (average polymerization degree=10) was analyzed, and, as a result, an absorption peak attributed to a carbodiimide group at a wavelength of about 2118 cm$^{-1}$ was confirmed by infrared (IR) spectrum measurement. The following could not be confirmed: absorption peaks attributed to an isocyanurate at absorption wavelengths: a wavelength of about 1710 cm$^{-1}$ and a wavelength of about 1411 cm$^{-1}$; absorption peaks attributed to a uretdione at absorption wavelengths: a wavelength of about 1765 cm$^{-1}$ and a wavelength of about 1410 cm$^{-1}$; and any absorption peak based on other by-product. Furthermore, GPC measurement was performed, and the polystyrene equivalent number average molecular weight was thus 1899.

The presence or absence of the carbodiimidization catalyst (alkali metal) was confirmed, thus absorption peaks attributed to an isocyanurate of the diphenylmethane diisocyanate at absorption wavelengths: a wavelength of about 1710 cm$^{-1}$ and a wavelength of about 1411 cm$^{-1}$; were observed, and it was thus confirmed that the catalyst remained.

Example 5

100 g of tetramethylxylylene diisocyanate and 0.5 g of an organic alkali metal having Lewis basicity (cesium acetate) as a carbodiimidization catalyst were placed in a 300-ml reaction container with a reflux tube and a stirrer and stirred under a nitrogen gas flow at 175° C. to perform a reaction until the result of NCO % measurement was 3.74%. The synthesis time was 21 hours. The resulting isocyanate-terminated polytetramethylxylylene carbodiimide (average polymerization degree=10) was analyzed, and, as a result, an absorption peak attributed to a carbodiimide group at a wavelength of about 2118 cm$^{-1}$ was confirmed by infrared (IR) spectrum measurement. The following could not be confirmed: absorption peaks attributed to an isocyanurate at absorption wavelengths: a wavelength of about 1710 cm$^{-1}$ and a wavelength of about 1411 cm$^{-1}$; absorption peaks attributed to a uretdione at absorption wavelengths: a wavelength of about 1765 cm$^{-1}$ and a wavelength of about 1410 cm$^{-1}$; and any absorption peak based on other by-product.

Furthermore, GPC measurement was performed, and the polystyrene equivalent number average molecular weight was thus 1904.

The presence or absence of the carbodiimidization catalyst (alkali metal) was confirmed, thus absorption peaks attributed to an isocyanurate of the diphenylmethane diisocyanate at absorption wavelengths: a wavelength of about 1710 cm$^{-1}$ and a wavelength of about 1411 cm$^{-1}$; were observed, and it was thus confirmed that the catalyst remained.

Example 6

100 g of tetramethylxylylene diisocyanate, 0.5 g of an organic alkali metal compound having Lewis basicity (potassium acetate) as a carbodiimidization catalyst, and 1.0 g of a phase transfer catalyst (18-crown 6-ether) were placed in a 300-ml reaction container with a reflux tube and a stirrer and stirred under a nitrogen gas flow at 175° C. to perform a reaction until the result of NCO % measurement was 3.74%. The synthesis time was 33 hours. The resulting isocyanate-terminated polytetramethylxylylene carbodiimide (average polymerization degree=10) was analyzed, and, as a result, an absorption peak attributed to a carbodiimide group at a wavelength of about 2118 cm$^{-1}$ was confirmed by infrared (IR) spectrum measurement. The following could not be confirmed: absorption peaks attributed to an isocyanurate at absorption wavelengths: a wavelength of about 1710 cm$^{-1}$ and a wavelength of about 1411 cm$^{-1}$; absorption peaks attributed to a uretdione at absorption wavelengths: a wavelength of about 1765 cm$^{-1}$ and a wavelength of about 1410 cm$^{-1}$; and any absorption peak based on other by-product. Furthermore, GPC measurement was performed, and the polystyrene equivalent number average molecular weight was thus 1955.

The presence or absence of the carbodiimidization catalyst (alkali metal) was confirmed, thus absorption peaks attributed to an isocyanurate of the diphenylmethane diisocyanate at absorption wavelengths: a wavelength of about 1710 cm$^{-1}$ and a wavelength of about 1411 cm$^{-1}$; were observed, and it was thus confirmed that the catalyst remained.

Example 7

100 g of tetramethylxylylene diisocyanate, 0.5 g of an organic alkali metal compound having Lewis basicity (potassium tert-butoxide) as a carbodiimidization catalyst, and 1.0 g of a phase transfer catalyst (tetrabutylammonium-2-ethylhexanoate) were placed in a 300-ml reaction container with a reflux tube and a stirrer and stirred under a nitrogen gas flow at 175° C. to perform a reaction until the result of NCO % measurement was 3.74%. The synthesis time was 20 hours. The resulting isocyanate-terminated polytetramethylxylylene carbodiimide (average polymerization degree=10) was analyzed, and, as a result, an absorption peak attributed to a carbodiimide group at a wavelength of about 2118 cm$^{-1}$ was confirmed by infrared (IR) spectrum measurement. The following could not be confirmed: absorption peaks attributed to an isocyanurate at absorption wavelengths: a wavelength of about 1710 cm$^{-1}$ and a wavelength of about 1411 cm$^{-1}$; absorption peaks attributed to a uretdione at absorption wavelengths: a wavelength of about 1765 cm$^{-1}$ and a wavelength of about 1410 cm$^{-1}$; and any absorption peak based on other by-product. Furthermore, GPC measurement was performed, and the polystyrene equivalent number average molecular weight was thus 1910.

The presence or absence of the carbodiimidization catalyst (alkali metal) was confirmed, thus absorption peaks attributed to an isocyanurate of the diphenylmethane diisocyanate at absorption wavelengths: a wavelength of about 1710 cm$^{-1}$ and a wavelength of about 1411 cm$^{-1}$; were observed, and it was thus confirmed that the catalyst remained.

Example 8

100 g of tetramethylxylylene diisocyanate, 0.5 g of an organic alkali metal compound having Lewis basicity (potassium tert-butoxide) as a carbodiimidization catalyst, and 1.0 g of a phase transfer catalyst (18-crown 6-ether) were placed in a 300-ml reaction container with a reflux tube and a stirrer and stirred under a nitrogen gas flow at 175° C. to perform a reaction until the result of NCO % measurement was 3.74%. The synthesis time was 2 hours. The resulting isocyanate-terminated polytetramethylxylylene carbodiimide (average polymerization degree=10) was analyzed, and, as a result, an absorption peak attributed to a carbodiimide group at a wavelength of about 2118 cm$^{-1}$ was confirmed by infrared (IR) spectrum measurement. The following could not be confirmed: absorption peaks attributed to an isocyanurate at absorption wavelengths: a wavelength of about 1710 cm$^{-1}$ and a wavelength of about 1411 cm$^{-1}$; absorption peaks attributed to a uretdione at absorption wavelengths: a wavelength of about 1765 cm$^{-1}$ and a wavelength of about 1410 cm$^{-1}$; and any absorption peak based on other by-product. Furthermore, GPC measurement was performed, and the polystyrene equivalent number average molecular weight was thus 1889.

The presence or absence of the carbodiimidization catalyst (alkali metal) was confirmed, thus absorption peaks attributed to an isocyanurate of the diphenylmethane diisocyanate at absorption wavelengths: a wavelength of about 1710 cm$^{-1}$ and a wavelength of about 1411 cm$^{-1}$; were observed, and it was thus confirmed that the catalyst remained.

Example 9

100 g of tetramethylxylylene diisocyanate, 0.5 g of an organic alkali metal compound having Lewis basicity (sodium ethoxide) as a carbodiimidization catalyst, and 1.0 g of a phase transfer catalyst (15-crown 5-ether) were placed in a 300-ml reaction container with a reflux tube and a stirrer and stirred under a nitrogen gas flow at 175° C. to perform a reaction until the result of NCO % measurement was 3.74%. The synthesis time was 2 hours. The resulting isocyanate-terminated polytetramethylxylylene carbodiimide (average polymerization degree=10) was analyzed, and, as a result, an absorption peak attributed to a carbodiimide group at a wavelength of about 2118 cm$^{-1}$ was confirmed by infrared (IR) spectrum measurement. The following could not be confirmed: absorption peaks attributed to an isocyanurate at absorption wavelengths: a wavelength of about 1710 cm$^{-1}$ and a wavelength of about 1411 cm$^{-1}$; absorption peaks attributed to a uretdione at absorption wavelengths: a wavelength of about 1765 cm$^{-1}$ and a wavelength of about 1410 cm$^{-1}$; and any absorption peak based on other by-product. Furthermore, GPC measurement was performed, and the polystyrene equivalent number average molecular weight was thus 1897.

The presence or absence of the carbodiimidization catalyst (alkali metal) was confirmed, thus absorption peaks attributed to an isocyanurate of the diphenylmethane diisocyanate at absorption wavelengths: a wavelength of about 1710 cm$^{-1}$ and a wavelength of about 1411 cm$^{-1}$; were observed, and it was thus confirmed that the catalyst remained.

Example 10

100 g of tetramethylxylylene diisocyanate, 0.5 g of an organic alkali metal compound having Lewis basicity (potassium tert-butoxide) as a carbodiimidization catalyst, and 1.0 g of a phase transfer catalyst (end-capped polyethylene glycol:polyoxyethylene dimethyl ether, number average molecular weight: 550) were placed in a 300-ml reaction container with a reflux tube and a stirrer and stirred under a nitrogen gas flow at 175° C. to perform a reaction until a time point where the result of NCO % measurement was 3.74%. The synthesis time was 11 hours. An isocyanate-terminated polytetramethylxylylene carbodiimide (average polymerization degree=10) was obtained. An absorption peak attributed to a carbodiimide group at a wavelength of about 2118 cm$^{-1}$ was confirmed by infrared (IR) spectrum measurement. The following could not be confirmed: absorption peaks attributed to an isocyanurate at absorption wavelengths: a wavelength of about 1710 cm$^{-1}$ and a wavelength of about 1411 cm$^{-1}$; absorption peaks attributed to a uretdione at absorption wavelengths: a wavelength of about 1765 cm$^{-1}$ and a wavelength of about 1410 cm$^{-1}$; and any absorption peak based on other by-product. Furthermore, GPC measurement was performed, and the polystyrene equivalent number average molecular weight was thus 1922.

The presence or absence of the carbodiimidization catalyst (alkali metal) was confirmed, thus absorption peaks attributed to an isocyanurate of the diphenylmethane diisocyanate at absorption wavelengths: a wavelength of about 1710 cm$^{-1}$ and a wavelength of about 1411 cm$^{-1}$; were observed, and it was thus confirmed that the catalyst remained.

Example 11

100 g of tetramethylxylylene diisocyanate, 0.5 g of an organic alkali metal compound having Lewis basicity (cesium acetate) as a carbodiimidization catalyst, and 1.0 g of a phase transfer catalyst (end-capped polyethylene glycol: polyoxyethylene dimethyl ether, number average molecular weight: 550) were placed in a 300-ml reaction container with a reflux tube and a stirrer and stirred under a nitrogen gas flow at 175° C. to perform a reaction until a time point where the result of NCO % measurement was 3.74%. The synthesis time was 10 hours. An isocyanate-terminated polytetramethylxylylene carbodiimide (average polymerization degree=10) was obtained. An absorption peak attributed to a carbodiimide group at a wavelength of about 2118 cm$^{-1}$ was confirmed by infrared (IR) spectrum measurement. The following could not be confirmed: absorption peaks attributed to an isocyanurate at absorption wavelengths: a wavelength of about 1710 cm$^{-1}$ and a wavelength of about 1411 cm$^{-1}$; absorption peaks attributed to a uretdione at absorption wavelengths: a wavelength of about 1765 cm$^{-1}$ and a wavelength of about 1410 cm$^{-1}$; and any absorption peak based on other by-product. Furthermore, GPC measurement was performed, and the polystyrene equivalent number average molecular weight was thus 1931.

The presence or absence of the carbodiimidization catalyst (alkali metal) was confirmed, thus absorption peaks attributed to an isocyanurate of the diphenylmethane diisocyanate at absorption wavelengths: a wavelength of about 1710 cm$^{-1}$ and a wavelength of about 1411 cm$^{-1}$; were observed, and it was thus confirmed that the catalyst remained.

Example 12

100 g of tetramethylxylylene diisocyanate and 1.0 g of polyoxyethylene monomethyl ether having a function like that of a phase transfer catalyst and having a number average molecular weight of 550 were placed in a 300-ml reaction container with a reflux tube and a stirrer and stirred under a nitrogen gas flow at 175° C. for 1 hour to allow a hydroxyl group as an end group of the polyoxyethylene monomethyl ether to react with the tetramethylxylylene diisocyanate by a urethanization reaction, and thereafter 0.5 g of an organic alkali metal compound having Lewis basicity (potassium tert-butoxide) as a carbodiimidization catalyst was loaded thereto to perform a reaction until a time point where the result of NCO % measurement was 3.66%. The synthesis time was 11 hours.

An isocyanate-terminated polytetramethylxylylene carbodiimide (average polymerization degree=10) was obtained (provided that the carbodiimide was partially end-capped with the polyoxyethylene monomethyl ether). An absorption peak attributed to a carbodiimide group at a wavelength of about 2118 cm$^{-1}$ was confirmed by infrared (IR) spectrum measurement. The following could not be confirmed: absorption peaks attributed to an isocyanurate at absorption wavelengths: a wavelength of about 1710 cm$^{-1}$ and a wavelength of about 1411 cm$^{-1}$; absorption peaks attributed to a uretdione at absorption wavelengths: a wavelength of about 1765 cm$^{-1}$ and a wavelength of about 1410 cm$^{-1}$; and any absorption peak based on other by-product. Furthermore, GPC measurement was performed, and the polystyrene equivalent number average molecular weight was thus 1924.

The presence or absence of the carbodiimidization catalyst (alkali metal) was confirmed, thus absorption peaks attributed to an isocyanurate of the diphenylmethane diisocyanate at absorption wavelengths: a wavelength of about 1710 cm$^{-1}$ and a wavelength of about 1411 cm$^{-1}$; were observed, and it was thus confirmed that the catalyst remained.

Example 13

100 g of tetramethylxylylene diisocyanate and 41 g of polyoxyethylene monomethyl ether (average molecular weight: 550) having a function like that of a phase transfer catalyst were placed in a 300-ml reaction container with a reflux tube and a stirrer and stirred under a nitrogen gas flow at 175° C. for 1 hour to react a hydroxyl group as an end group of the polyoxyethylene monomethyl ether with the tetramethylxylylene diisocyanate by a urethanization reaction. (Molar ratio between tetramethylxylylene diisocyanate and polyoxyethylene monomethyl ether: 11:2.) Subsequently, 0.5 g of an organic alkali metal compound having Lewis basicity (potassium tert-butoxide) as a carbodiimidization catalyst was loaded thereto and stirred to perform a reaction until any absorption of an isocyanate group at a wavelength of 2200 to 2300 cm$^{-1}$ disappeared in infrared (IR) spectrum measurement. The synthesis time was 8 hours. The resulting polyoxyethylene monomethyl ether-terminated polycarbodiimide (average polymerization degree: 10) was analyzed, and, as a result, an absorption peak attributed to a carbodiimide group at a wavelength of about 2118 cm$^{-1}$ was confirmed by infrared (IR) spectrum measurement. The following could not be confirmed:

absorption peaks attributed to an isocyanurate at absorption wavelengths: a wavelength of about 1710 cm$^{-1}$ and a wavelength of about 1411 cm$^{-1}$; absorption peaks attributed to a uretdione at absorption wavelengths: a wavelength of about 1765 cm$^{-1}$ and a wavelength of about 1410 cm$^{-1}$; and any absorption peak based on other by-product. Furthermore, GPC measurement was performed, and the polystyrene equivalent number average molecular weight was thus 2320.

The presence or absence of the carbodiimidization catalyst (alkali metal) was confirmed, thus absorption peaks attributed to an isocyanurate of the diphenylmethane diisocyanate at absorption wavelengths: a wavelength of about 1710 cm$^{-1}$ and a wavelength of about 1411 cm$^{-1}$; were observed, and it was thus confirmed that the catalyst remained.

Example 14

100 g of tetramethylxylylene diisocyanate and 41 g of polyoxyethylene monomethyl ether (average molecular weight: 550) having a function like that of a phase transfer catalyst were placed in a 300-ml reaction container with a reflux tube and a stirrer and stirred under a nitrogen gas flow at 175° C. for 1 hour to react a hydroxyl group as an end group of the polyoxyethylene monomethyl ether with the tetramethylxylylene diisocyanate by a urethanization reaction. (Molar ratio between tetramethylxylylene diisocyanate and polyoxyethylene monomethyl ether: 11:2.) Subsequently, 0.5 g of an organic alkali metal compound having Lewis basicity (potassium tert-butoxide) as a carbodiimidization catalyst and 1.0 g of a phase transfer catalyst (tetrabutylammonium-2-ethylhexanoate) were loaded thereto and stirred to perform a reaction until any absorption of an isocyanate group at a wavelength of 2200 to 2300 cm$^{-1}$ disappeared in infrared (IR) spectrum measurement. The synthesis time was 4.5 hours. The resulting polyoxyethylene monomethyl ether-terminated polycarbodiimide (average polymerization degree: 10) was analyzed, and, as a result, an absorption peak attributed to a carbodiimide group at a wavelength of about 2118 cm$^{-1}$ was confirmed by infrared (IR) spectrum measurement. The following could not be confirmed: absorption peaks attributed to an isocyanurate at absorption wavelengths: a wavelength of about 1710 cm$^{-1}$ and a wavelength of about 1411 cm$^{-1}$; absorption peaks attributed to a uretdione at absorption wavelengths: a wavelength of about 1765 cm$^{-1}$ and a wavelength of about 1410 cm$^{-1}$; and any absorption peak based on other by-product. Furthermore, GPC measurement was performed, and the polystyrene equivalent number average molecular weight was thus 2350.

The presence or absence of the carbodiimidization catalyst (alkali metal) was confirmed, thus absorption peaks attributed to an isocyanurate of the diphenylmethane diisocyanate at absorption wavelengths: a wavelength of about 1710 cm$^{-1}$ and a wavelength of about 1411 cm$^{-1}$; were observed, and it was thus confirmed that the catalyst remained.

Example 15

100 g of tetramethylxylylene diisocyanate and 41 g of polyoxyethylene monomethyl ether (average molecular weight: 550) having a function like that of a phase transfer catalyst were placed in a 300-ml reaction container with a reflux tube and a stirrer and stirred under a nitrogen gas flow at 175° C. for 1 hour to react a hydroxyl group as an end group of the polyoxyethylene monomethyl ether with the tetramethylxylylene diisocyanate by a urethanization reaction. (Molar ratio between tetramethylxylylene diisocyanate and polyoxyethylene monomethyl ether: 11:2.) Subsequently, 0.5 g of an organic alkali metal compound having Lewis basicity (potassium tert-butoxide) as a carbodiimidization catalyst and 1.0 g of a phase transfer catalyst (18-crown 6-ether) were loaded thereto and stirred to perform a reaction until any absorption of an isocyanate group at a wavelength of 2200 to 2300 cm$^{-1}$ disappeared in infrared (IR) spectrum measurement. The synthesis time was 4.5 hours. The resulting polyoxyethylene monomethyl ether-terminated polycarbodiimide (average polymerization degree: 10) was analyzed, and, as a result, an absorption peak attributed to a carbodiimide group at a wavelength of about 2118 cm$^{-1}$ was confirmed by infrared (IR) spectrum measurement. The following could not be confirmed: absorption peaks attributed to an isocyanurate at absorption wavelengths: a wavelength of about 1710 cm$^{-1}$ and a wavelength of about 1411 cm$^{-1}$; absorption peaks attributed to a uretdione at absorption wavelengths: a wavelength of about 1765 cm$^{-1}$ and a wavelength of about 1410 cm$^{-1}$; and any absorption peak based on other by-product. Furthermore, GPC measurement was performed, and the polystyrene equivalent number average molecular weight was thus 2385.

The presence or absence of the carbodiimidization catalyst (alkali metal) was confirmed, thus absorption peaks attributed to an isocyanurate of the diphenylmethane diisocyanate at absorption wavelengths: a wavelength of about 1710 cm$^{-1}$ and a wavelength of about 1411 cm$^{-1}$; were observed, and it was thus confirmed that the catalyst remained.

Example 16

100 g of tetramethylxylylene diisocyanate and 41 g of polyoxyethylene monomethyl ether (average molecular weight: 550) having a function like that of a phase transfer catalyst were placed in a 300-ml reaction container with a reflux tube and a stirrer and stirred under a nitrogen gas flow at 175° C. for 1 hour to react a hydroxyl group as an end group of the polyoxyethylene monomethyl ether with the tetramethylxylylene diisocyanate by a urethanization reaction. (Molar ratio between tetramethylxylylene diisocyanate and polyoxyethylene monomethyl ether: 11:2.) Subsequently, 0.5 g of an organic alkali metal compound having Lewis basicity (potassium tert-butoxide) as a carbodiimidization catalyst and 1.0 g of a phase transfer catalyst (tetrabutylammonium-2-ethylhexanoate) were loaded thereto and stirred to perform a reaction until any absorption of an isocyanate group at a wavelength of 2200 to 2300 cm$^{-1}$ disappeared in infrared (IR) spectrum measurement. The synthesis time was 4.5 hours. Thereafter, 2.5 g of "Kyowaad 600S" (manufactured by Kyowa Chemical Industry Co., Ltd.: $2MgO \cdot 6SiO_2 \cdot mH_2O$) as a synthetic magnesium silicate-based adsorbent was loaded in the reaction container, and stirred under a nitrogen gas flow at 150° C. for 2 hours. Next, suction filtration was performed with a glass suction filter, and polyoxyethylene monomethyl ether-terminated polycarbodiimide (average polymerization degree: 10) after catalyst adsorption was obtained. The resulting polyoxyethylene monomethyl ether-terminated polycarbodiimide (average polymerization degree: 10) was analyzed, and, as a result, an absorption peak attributed to a carbodiimide group at a wavelength of about 2118 cm$^{-1}$ was confirmed by infrared (IR) spectrum measurement. The following could not be confirmed: absorption peaks attributed to an isocyanurate at absorption wavelengths: a wavelength of about 1710 cm$^{-1}$ and a wavelength of about 1411 cm$^{-1}$; absorption peaks attributed to a uretdione at absorption wavelengths: a wavelength of about 1765 cm$^{-1}$ and a wavelength of about 1410 cm$^{-1}$; and any absorption peak based on other by-product. Furthermore, GPC measurement was performed, and the polystyrene equivalent number average molecular weight was thus 2360.

The presence or absence of the carbodiimidization catalyst (alkali metal) was confirmed, and no change in absorption peak was thus confirmed immediately after the mixing and after the mixing and heating and sufficient removal of the catalyst was confirmed.

Reference Example 1

100 g of tetramethylxylylene diisocyanate and 0.5 g of 3-methyl-1-phenyl-2-phospholene-1-oxide being a phosphorus compound as a carbodiimidization catalyst were placed in a 300-ml reaction container with a reflux tube and a stirrer and stirred under a nitrogen gas flow at 175° C. to perform a reaction until the result of NCO % measurement was 3.74%. The synthesis time was 26 hours. The resulting isocyanate-terminated polytetramethylxylylene carbodiimide (average polymerization degree=10) was analyzed, and, as a result, an absorption peak attributed to a carbodiimide group at a wavelength of about 2118 cm$^{-1}$ was confirmed by infrared (IR) spectrum measurement. The following could not be confirmed: absorption peaks attributed to an isocyanurate at absorption wavelengths: a wavelength of about 1710 cm$^{-1}$ and a wavelength of about 1411 cm$^{-1}$; absorption peaks attributed to a uretdione at absorption wavelengths: a wavelength of about 1765 cm$^{-1}$ and a wavelength of about 1410 cm$^{-1}$; and any absorption peak based on other by-product. Furthermore, GPC measurement was performed, and the polystyrene equivalent number average molecular weight was thus 1896.

The presence or absence of the carbodiimidization catalyst (alkali metal) was confirmed, and it was thus confirmed that the catalyst remained, because decarboxylation due to carbodiimidization of diphenylmethane diisocyanate was observed during heating and absorption peaks at an absorption wavelength of 2138 cm$^{-1}$ and a wavelength of about 2112 cm$^{-1}$ were observed by infrared (IR) spectrum measurement.

Reference Example 2

100 g of tetramethylxylylene diisocyanate and 0.5 g of 3-methyl-1-phenyl-2-phospholene-1-oxide being a phosphorus compound as a carbodiimidization catalyst were placed in a 300-ml reaction container with a reflux tube and a stirrer and stirred under a nitrogen gas flow at 195° C. to perform a reaction until a time point where the result of NCO % measurement was 3.74%. The synthesis time was 12 hours. The resulting isocyanate-terminated polytetramethylxylylene carbodiimide (average polymerization degree=10) was analyzed, and, as a result, an absorption peak attributed to a carbodiimide group at a wavelength of about 2118 cm$^{-1}$ was confirmed by infrared (IR) spectrum measurement. The following could not be confirmed: absorption peaks attributed to an isocyanurate at absorption wavelengths: a wavelength of about 1710 cm$^{-1}$ and a wavelength of about 1411 cm$^{-1}$; absorption peaks attributed to a uretdione at absorption wavelengths: a wavelength of about 1765 cm$^{-1}$ and a wavelength of about 1410 cm$^{-1}$; and any absorption peak based on other by-product. Furthermore, GPC measurement was performed and the polystyrene equivalent number average molecular weight was thus 1020, and it was thus confirmed that isocyanate by itself was decomposed under a high temperature and no carbodiimidization reaction smoothly progressed.

The presence or absence of the carbodiimidization catalyst (alkali metal) was confirmed, and it was thus confirmed that the catalyst remained, because decarboxylation due to carbodiimidization of diphenylmethane diisocyanate was observed during heating and absorption peaks at an absorption wavelength of 2138 cm$^{-1}$ and a wavelength of about 2112 cm$^{-1}$ were observed by infrared (IR) spectrum measurement.

Comparative Example 1

100 g of hexamethylene diisocyanate (primary isocyanate) and 0.5 g of an organic alkali metal compound having Lewis basicity (potassium tert-butoxide) as a carbodiimidization catalyst were placed in a 300-ml reaction container with a reflux tube and a stirrer and stirred under a nitrogen gas flow at 175° C., but the content was gelated at a time point after a lapse of 3 hours. The resulting reaction product was analyzed by infrared (IR) spectrum measurement, and, as a result, an absorption peak attributed to a carbodiimide group at a wavelength of about 2125 cm$^{-1}$ and absorption peaks attributed to an isocyanurate group at a wavelength of about 1710 cm$^{-1}$ and a wavelength of about 1411 cm$^{-1}$ were confirmed. The resulting substance was gelated and could not be thus subjected to GPC measurement.

The presence or absence of the carbodiimidization catalyst (alkali metal) could not also be confirmed because the resulting substance was gelated and could not be thus subjected to measurement.

Comparative Example 2

100 g of 4,4'-dicyclohexylmethane diisocyanate (secondary isocyanate) and 0.5 g of an organic alkali metal compound having Lewis basicity (potassium tert-butoxide) as a carbodiimidization catalyst were placed in a 300-ml reaction container with a reflux tube and a stirrer and stirred under a nitrogen gas flow at 175° C., but the content was gelated at a time point after a lapse of 3 hours. The resulting reaction product was analyzed by infrared (IR) spectrum measurement, and, as a result, an absorption peak attributed to a carbodiimide group at a wavelength of about 2120 cm$^{-1}$ and absorption peaks attributed to an isocyanurate group at a wavelength of about 1710 cm$^{-1}$ and a wavelength of about 1411 cm$^{-1}$ were confirmed. The resulting substance was gelated and could not be thus subjected to GPC measurement.

The presence or absence of the carbodiimidization catalyst (alkali metal) could not also be confirmed because the resulting substance was gelated and could not be thus subjected to measurement.

Comparative Example 3

100 g of phenylisocyanate and 0.5 g of an organic alkali metal compound having Lewis basicity (potassium tert-butoxide) as a carbodiimidization catalyst were placed in a 300-ml reaction container with a reflux tube and a stirrer and stirred under a nitrogen gas flow at 120° C. to perform a reaction until any absorption of an isocyanate group at a wavelength of 2200 to 2300 cm$^{-1}$ disappeared in infrared (IR) spectrum measurement. The synthesis time was 0.5 hours. The resulting reaction product was analyzed by infrared (IR) spectrum measurement, and, as a result, absorption peaks attributed to a carbodiimide group at a wavelength of about 2121 cm$^{-1}$ and a wavelength of about 2102 cm$^{-1}$ could not be confirmed and absorption peaks attributed to an isocyanurate group at a wavelength of about 1710 cm$^{-1}$ and a wavelength of about 1411 cm$^{-1}$ were confirmed. The resulting substance was insoluble in a THF solvent, and could not be thus subjected to molecular weight measurement by GPC.

The presence or absence of the carbodiimidization catalyst (alkali metal) could not also be determined because the resulting substance was insoluble in diphenylmethane diisocyanate and could not be thus subjected to measurement.

Reference Example 3

100 g of tetramethylxylylene diisocyanate and 41 g of polyoxyethylene monomethyl ether (average molecular weight: 550) were placed in a 300-ml reaction container with a reflux tube and a stirrer and stirred under a nitrogen gas flow at 175° C. for 1 hour to react a hydroxyl group as an end group of the polyoxyethylene monomethyl ether with the tetramethylxylylene diisocyanate by a urethanization reaction. (Molar ratio between tetramethylxylylene diisocyanate and polyoxyethylene monomethyl ether: 11:2.) Subsequently, 0.5 g of 3-methyl-1-phenyl-2-phospholene-1-oxide being a phosphorus compound as a carbodiimidization catalyst was loaded thereto and stirred to perform a reaction until any absorption of an isocyanate group at a wavelength of 2200 to 2300 cm$^{-1}$ disappeared in infrared (IR) spectrum measurement. The synthesis time was 52 hours. The resulting polyoxyethylene monomethyl ether-terminated polycarbodiimide (average polymerization degree: 10) was analyzed, and, as a result, an absorption peak attributed to a carbodiimide group at a wavelength of about 2118 cm$^{-1}$ was confirmed by infrared (IR) spectrum measurement. The following could not be confirmed: absorption peaks attributed to an isocyanurate at absorption wavelengths: a wavelength of about 1710 cm$^{-1}$ and a wavelength of about 1411 cm$^{-1}$; absorption peaks attributed to a uretdione at absorption wavelengths: a wavelength of about 1765 cm$^{-1}$ and a wavelength of about 1410 cm$^{-1}$; and any absorption peak based on other by-product. Furthermore, GPC measurement was performed, and the polystyrene equivalent number average molecular weight was thus 2377.

The presence or absence of the carbodiimidization catalyst (alkali metal) was confirmed, and it was thus confirmed that the catalyst remained, because decarboxylation due to carbodiimidization of diphenylmethane diisocyanate was observed during heating and absorption peaks at an absorption wavelength of 2138 cm$^{-1}$ and a wavelength of about 2112 cm$^{-1}$ were observed by infrared (IR) spectrum measurement.

Comparative Example 4

100 g of tetramethylxylylene diisocyanate and 0.5 g of an alkali earth metal compound having Lewis basicity (magnesium ethoxide) as a carbodiimidization catalyst were placed in a 300-ml reaction container with a reflux tube and a stirrer and stirred under a nitrogen gas flow at 175° C. for 26 hours, and the NCO % was measured and was 34.20%.

The resulting content was analyzed, and, as a result, an absorption peak attributed to a carbodiimide group at a wavelength of about 2118 cm$^{-1}$ could not be confirmed by infrared (IR) spectrum measurement. The following could not also be confirmed: absorption peaks attributed to an isocyanurate at absorption wavelengths: a wavelength of about 1710 cm$^{-1}$ and a wavelength of about 1411 cm$^{-1}$; absorption peaks attributed to a uretdione at absorption wavelengths: a wavelength of about 1765 cm$^{-1}$ and a wavelength of about 1410 cm$^{-1}$; and any absorption peak based on other by-product.

Gas chromatograph mass spectrometry (GC-MS)

Each carbodiimide compound obtained in Examples, Comparative Examples, and Reference Examples was subjected to quantitative analysis by gas chromatograph mass spectrometry (GC-MS) in the following conditions. The results are shown in Table 2.

[Measurement Conditions of GC-MS]
Column: HP-5 (manufactured by Agilent Technologies, inner diameter: 0.32 mm, thickness: 0.25 μm, length: 30 m)
Carrier gas: helium, 1.0 mL/min
Injection conditions: 250° C., split ratio: 1/50
Detection conditions: FID system, 220° C.
Column temperature conditions: retention at 40° C. for 5 minutes and then temperature rise to 350° C. at 10° C./min
Ionization mode: EI
Temperature of ion source: 230° C.
Temperature of interface: 350° C.

TABLE 1

| | Isocyanate | | | | | Carbodiimidization catalyst | | | | | | Phosphorus |
|---|---|---|---|---|---|---|---|---|---|---|---|---|
| | (A) Tertiary isocyanate | | Other than tertiary isocyanate | | | (B) | | | | | | |
| | | | Primary | Secondary | Aromatic | | | | | | | |
| | TMXDI (9) | TMI (g) | HDI (g) | HMDI (g) | Ph-Iso (g) | PTB (g) | EtONa (g) | LDA (g) | CsAc (g) | KAc (g) | EtOMg (g) | MPO (g) |
| Example 1 | 100 | | | | | 0.5 | | | | | | |
| Example 2 | | 100 | | | | 0.5 | | | | | | |
| Example 3 | 100 | | | | | | 0.5 | | | | | |
| Example 4 | 100 | | | | | | | 0.5 | | | | |
| Example 5 | 100 | | | | | | | | 0.5 | | | |
| Example 6 | 100 | | | | | | | | | 0.5 | | |
| Example 7 | 100 | | | | | 0.5 | | | | | | |
| Example 8 | 100 | | | | | 0.5 | | | | | | |
| Example 9 | 100 | | | | | | | 0.5 | | | | |
| Example 10 | 100 | | | | | 0.5 | | | | | | |
| Example 11 | 100 | | | | | | | | | 0.5 | | |
| Example 12 | 100 | | | | | 0.5 | | | | | | |

TABLE 1-continued

| | | | | | |
|---|---|---|---|---|---|
| Example 13 | 100 | | | 0.5 | |
| Example 14 | 100 | | | 0.5 | |
| Example 15 | 100 | | | 0.5 | |
| Example 16 | 100 | | | 0.5 | |
| Reference Example 1 | 100 | | | | 0.5 |
| Reference Example 2 | 100 | | | | 0.5 |
| Comparative Example 1 | | 100 | | 0.5 | |
| Comparative Example 2 | | | 100 | 0.5 | |
| Comparative Example 3 | | | | 100 | 0.5 |
| Reference Example 3 | 100 | | | | 0.5 |
| Comparative Example 4 | 100 | | | | 0.5 |

| | Phase transfer catalyst (C) | | | End-capping | | Synthesis conditions | |
|---|---|---|---|---|---|---|---|
| | 18-Crown (g) | 15-Crown (g) | 18X (g) | PEG end-capped (g) | agent (D-1) MP550 (g) | Adsorbent (E) 600S (g) | Synthesis temperature (° C.) | Synthesis time (hr) |
| Example 1 | | | | | | | 175 | 26 |
| Example 2 | | | | | | | 175 | 45 |
| Example 3 | | | | | | | 175 | 21 |
| Example 4 | | | | | | | 175 | 10 |
| Example 5 | | | | | | | 175 | 21 |
| Example 6 | 1 | | | | | | 175 | 33 |
| Example 7 | | 1 | | | | | 175 | 20 |
| Example 8 | 1 | | | | | | 175 | 2 |
| Example 9 | | 1 | | | | | 175 | 2 |
| Example 10 | | | 1 | | | | 175 | 11 |
| Example 11 | | | 1 | | | | 175 | 10 |
| Example 12 | | | | 1 | | | 175 | 11 |
| Example 13 | | | | | 41 | | 175 | 8 |
| Example 14 | | 1 | | | 41 | | 175 | 4.5 |
| Example 15 | 1 | | | | 41 | | 175 | 4.5 |
| Example 16 | | | 1 | | 41 | 2.5 | 175 | 4.5 |
| Reference Example 1 | | | | | | | 175 | 26 |
| Reference Example 2 | | | | | | | 195 | 12 |
| Comparative Example 1 | | | | | | | 175 | Gelation |
| Comparative Example 2 | | | | | | | 175 | Gelation |
| Comparative Example 3 | | | | | | | 120 | 0.5 |
| Reference Example 3 | | | | | 41 | | 175 | 52 |
| Comparative Example 4 | | | | | | | 175 | 26 |

Notations in Table 1 are as follows.
TMXDI: tetramethylxylylene diisocyanate
TMI: 3-isopropenyl-α,α-dimethylbenzyl isocyanate
HDI: hexamethylene diisocyanate
HMDI: 4,4'-dicyclohexylmethane diisocyanate
Ph-Iso: phenylisocyanate
PTB: potassium tert-butoxide
EtONa: sodium ethoxide
LDA: lithium diisopropylamide
sAc: cesium acetate
EtOMg: magnesium ethoxide
KAc: potassium acetate
MPO: 3-methyl-1-phenyl-2-phospholene-1-oxide
18-Crown: 18-crown 6-ether
15-Crown: 15-crown 5-ether
18X: tetrabutylammonium-2-ethylhexanoate
PEG end-capped: polyoxyethylene dimethyl ether (number average molecular weight 550)
MP550: polyoxyethylene monomethyl ether (number average molecular weight: 550)
600S: $2MgO \cdot 6SiO_2 \cdot mH_2O$

TABLE 2

| | Determination by FT-IR | | | NCO (%) | Average polymerization degree | Mn | Presence or absence of absorption wavelength with respect to isocyanurate | Amount of carbodiimidization catalyst (alkali metal) remaining in carbodiimide obtained (*1) | Amount of carbodiimidization catalyst (phospholene oxides) remaining in carbodiimide obtained (*1) |
|---|---|---|---|---|---|---|---|---|---|
| | Carbodiimide | Dimer | Trimer | | | | | | |
| Example 1 | Presence | Absence | Absence | 3.74 | 10 | 1891 | Presence | 1877 ppm (as K) | Not detected (*2) |
| Example 2 | Presence | Absence | Absence | 0 | 1 | 145 | Presence | 1991 ppm (as K) | Not detected (*2) |
| Example 3 | Presence | Absence | Absence | 3.74 | 10 | 1886 | Presence | 1866 ppm (as Na) | Not detected (*2) |
| Example 4 | Presence | Absence | Absence | 3.74 | 10 | 1899 | Presence | 1796 ppm (as Li) | Not detected (*2) |
| Example 5 | Presence | Absence | Absence | 3.74 | 10 | 1904 | Presence | 1955 ppm (as Cs) | Not detected (*2) |
| Example 6 | Presence | Absence | Absence | 3.74 | 10 | 1955 | Presence | 1807 ppm (as K) | Not detected (*2) |
| Example 7 | Presence | Absence | Absence | 3.74 | 10 | 1910 | Presence | 1844 ppm (as K) | Not detected (*2) |
| Example 8 | Presence | Absence | Absence | 3.74 | 10 | 1889 | Presence | 1811 ppm (as K) | Not detected (*2) |
| Example 9 | Presence | Absence | Absence | 3.74 | 10 | 1897 | Presence | 1845 ppm (as Na) | Not detected (*2) |
| Example 10 | Presence | Absence | Absence | 3.74 | 10 | 1922 | Presence | 1827 ppm (as K) | Not detected (*2) |
| Example 11 | Presence | Absence | Absence | 3.74 | 10 | 1931 | Presence | 1987 ppm (as Cs) | Not detected (*2) |
| Example 12 | Presence | Absence | Absence | 3.66 | 10 | 1924 | Presence | 1853 ppm (as K) | Not detected (*2) |
| Example 13 | Presence | Absence | Absence | 0 | 10 | 2320 | Presence | 1356 ppm (as K) | Not detected (*2) |
| Example 14 | Presence | Absence | Absence | 0 | 10 | 2350 | Presence | 1320 ppm (as K) | Not detected (*2) |
| Example 15 | Presence | Absence | Absence | 0 | 10 | 2385 | Presence | 1239 ppm (as K) | Not detected (*2) |
| Example 16 | Presence | Absence | Absence | 0 | 10 | 2360 | Absence | 155 ppm (as K) | Not detected (*2) |
| Reference Example 1 | Presence | Absence | Absence | 3.74 | 10 | 1896 | Absence | 100 ppm or less (as alkali metal) | 100 ppm or more (as phospholene oxides) |
| Reference Example 2 | Presence | Absence | Absence | 3.74 | 10 | 1020 | Absence | 100 ppm or less (as alkali metal) | 100 ppm or more (as phospholene oxides) |
| Comparative Example 1 | Presence | Absence | Presence | — | — | Unmeasurable | Unmeasurable | Unmeasurable | Unmeasurable |
| Comparative Example 2 | Presence | Absence | Presence | — | — | Unmeasurable | Unmeasurable | Unmeasurable | Unmeasurable |
| Comparative Example 3 | Absence | Absence | Presence | 0 | — | Unmeasurable | Unmeasurable | Unmeasurable | Unmeasurable |
| Reference Example 3 | Presence | Absence | Absence | 0 | 10 | 2377 | Absence | 100 ppm or less (as alkali metal) | 100 ppm or more (as phospholene oxides) |
| Comparative Example 4 | Absence | Absence | Absence | 34.2 | — | — | — | — | — |

(*1): "ppm" means "ppm by mass".
(*2): "Not detected" means any value less than a detection limit value of 1 ppm by mass.

Each carbodiimide compound could be obtained in Examples 1 to 16, and the phase transfer catalyst (C) or the end-capping agent (D-1) was used to result in a decrease in time taken for carbodiimidization in Examples 6 to 16.

Neither a dimer, nor a trimer was detected in the resulting carbodiimide compound.

On the other hand, other isocyanate compound was compounded instead of the aliphatic tertiary isocyanate compound (A) to cause gelation in Comparative Examples 1 to 2.

Other isocyanate compound was compounded instead of the aliphatic tertiary isocyanate compound (A) and thus no carbodiimide compound could be obtained in Comparative Example 3.

Magnesium ethoxide was compounded instead of the organic alkali metal compound (B) and thus no carbodiimide compound could be obtained in Comparative Example 4.

The catalyst could be removed by a simple operation, as in Example 16.

Examples 17 to 26

Each carbodiimide compound shown in Table 3 was added to a mixed solution of a polyester-based polyurethane resin (Elastollan XNY585N-10 (manufactured by BASF SE)) dissolved in DMF/THF so that the compounding ratio (solid content (active component) equivalent) shown in Table 3 was achieved, thereby obtaining each polyester-based polyurethane resin composition (solution).

A PET film release-treated by a Control Coater IMC-7013 model was coated with the solution and dried at 80° C. for 5 hours to obtain a 100-μm resin sheet. The resin sheet was formed into a strip sheet having a width of 10 mm and a length of 70 mm.

The tensile strength of the strip sheet was measured by a tensile tester ("3365" manufactured by Instron).

The strip sheet was mounted in a highly accelerated life test apparatus ("PH-2KT-E", thermo-hygrostat manufactured by Espec Corp.; temperature 80° C., relative humidity 95%) and subjected to a moist heat treatment for 15 days. The tensile strength of the strip sheet after the moist heat treatment was measured by the tensile tester.

The respective average values of the tensile strengths of five strip sheets before and after the moist heat treatment were calculated, and the strength retention ratio of the average value of the tensile strengths after the treatment to the average value of the tensile strengths before the treatment was calculated.

The results are shown in Table 3.

Comparative Example 5

A strip sheet was produced in the same manner as in Example 17 except that no carbodiimide compound was added to a mixed solution of a polyester-based polyurethane resin (Elastollan XNY585N-10 (manufactured by BASF SE)) dissolved in DMF/THF, and was subjected to the same tests as in Example 17.

The results are shown in Table 3.

TABLE 3

| | Polyester-based polyurethane resin composition | | | Characteristic evaluation Strength retention ratio (hydrolysis resistance) 80° C., 95% RH |
|---|---|---|---|---|
| | Polyester-based polyurethane resin parts by mass | Carbodiimide compound Type | parts by mass | 20 days % |
| Example 17 | 99 | Example 1 | 1 | 81 |
| Example 18 | 98 | Example 1 | 2 | 90 |
| Example 19 | 99 | Example 2 | 1 | 14 |
| Example 20 | 98 | Example 2 | 2 | 60 |
| Example 21 | 99 | Example 8 | 1 | 80 |
| Example 22 | 98 | Example 8 | 2 | 89 |
| Example 23 | 99 | Example 13 | 1 | 65 |
| Example 24 | 98 | Example 13 | 2 | 78 |
| Example 25 | 99 | Example 16 | 1 | 68 |
| Example 26 | 98 | Example 16 | 2 | 81 |
| Comparative Example 5 | 100 | — | — | 9 |

As clear from Table 3, the resin sheet obtained with the polyester-based polyurethane resin composition to which the carbodiimide compound was compounded was excellent in hydrolysis resistance.

The invention claimed is:

1. A method for producing a carbodiimide compound, comprising:
   a carbodiimide production step of reacting an aliphatic tertiary isocyanate compound (A) in the presence of an organic alkali metal compound (B) having Lewis basicity, and
   an adsorption and removal step of performing adsorption and removal of the organic alkali metal compound (B) having Lewis basicity, with an adsorbent (E), after the carbodiimide production step; and
   wherein the adsorbent (E) is at least one of a synthetic aluminum silicate-based adsorbent, synthetic magnesium silicate, an acidic cation-exchange resin, a basic anion-exchange resin, alumina, a silica gel-based adsorbent, a zeolite-based adsorbent, hydrotalcites, a magnesium oxide-aluminum oxide-based solid solution, aluminum hydroxide, magnesium oxide, and an aluminum hydroxide-sodium hydrogen carbonate coprecipitate (dawsonite).

2. The method for producing a carbodiimide compound according to claim 1, wherein the organic alkali metal compound (B) having Lewis basicity is at least one of a metal alkoxide, a metal amide, and a metal carboxylate.

3. The method for producing a carbodiimide compound according to claim 1, wherein the aliphatic tertiary isocyanate compound (A) is a compound in which at least one aromatic ring is bonded to a tertiary carbon atom to which an isocyanate group is bonded.

4. The method for producing a carbodiimide compound according to claim 1, wherein the aliphatic tertiary isocyanate compound (A) is at least one of tetramethylxylylene diisocyanate and 3-isopropenyl-α,α-dimethylbenzyl isocyanate.

5. The method for producing a carbodiimide compound according to claim 1, wherein the aliphatic tertiary isocyanate compound (A) is reacted in the presence of the organic alkali metal compound (B) having Lewis basicity and a phase transfer catalyst (C) in the carbodiimide production step.

6. The method for producing a carbodiimide compound according to claim 5, wherein the phase transfer catalyst (C) is at least one of crown ether, a quaternary ammonium salt, and a compound represented by the following general formula (1):

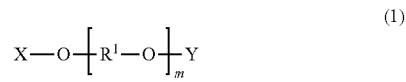
(1)

wherein X and Y are each independently a methyl group, an ethyl group, a propyl group, a butyl group, or a phenyl group; $R^1$ is an alkylene group having 2 to 3 carbon atoms; and m is an integer of 2 to 500.

7. The method for producing a carbodiimide compound according to claim 1, wherein the method comprises an end-capping step of end-capping a portion of an isocyanate group in the aliphatic tertiary isocyanate compound (A) with an end-capping agent at at least one time point among three time points, before the carbodiimide production step, during the production step, and after the production step, and the end-capping agent is a compound (D-1) represented by the following general formula (2-1):

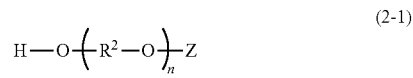
(2-1)

wherein Z is a methyl group, an ethyl group, a propyl group, a butyl group, or a phenyl group; $R^2$ is an alkylene group having 2 to 3 carbon atoms; and n is an integer of 2 to 500.

8. The method for producing a carbodiimide compound according to claim 1, wherein the method comprises a chain extension step of reacting a portion of an isocyanate group in the aliphatic tertiary isocyanate compound (A) with a chain extender at at least one time point among three time points, before the carbodiimide production step, during the production step, and after the production step, and the chain extender is a compound (D-2) represented by the following general formula (2-2):

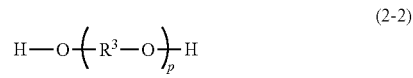
(2-2)

wherein $R^3$ is an alkylene group having 2 to 3 carbon atoms; and p is an integer of 2 to 500.

* * * * *